US011241414B2

(12) United States Patent
Cartt et al.

(10) Patent No.: US 11,241,414 B2
(45) Date of Patent: *Feb. 8, 2022

(54) ADMINISTRATION OF BENZODIAZEPINE COMPOSITIONS

(71) Applicant: Neurelis, Inc., San Diego, CA (US)

(72) Inventors: Steve Cartt, Hillsborough, CA (US); David Medeiros, Sparks, NV (US); Garry Thomas Gwozdz, Jim Thorpe, PA (US); Andrew Loxley, Brussels (BE); Mark Mitchnick, East Hampton, NY (US); David F. Hale, San Diego, CA (US); Edward T. Maggio, San Diego, CA (US)

(73) Assignee: Neurelis, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/332,800

(22) Filed: May 27, 2021

(65) Prior Publication Data

US 2021/0299089 A1 Sep. 30, 2021

Related U.S. Application Data

(63) Continuation of application No. 17/228,514, filed on Apr. 12, 2021, which is a continuation of application No. 15/955,397, filed on Apr. 17, 2018, now abandoned, which is a continuation of application No. 12/413,439, filed on Mar. 27, 2009, now abandoned.

(60) Provisional application No. 61/040,558, filed on Mar. 28, 2008.

(51) Int. Cl.
*A61K 31/355* (2006.01)
*A61K 9/00* (2006.01)
*A61K 31/5513* (2006.01)

(52) U.S. Cl.
CPC ............ *A61K 31/355* (2013.01); *A61K 9/008* (2013.01); *A61K 9/0043* (2013.01); *A61K 31/5513* (2013.01)

(58) Field of Classification Search
CPC .............. A61K 31/355; A61K 31/5513; A61K 9/0043; A61K 9/5513
See application file for complete search history.

(56) References Cited

U.S. PATENT DOCUMENTS

| | | |
|---|---|---|
| 3,102,116 A | 8/1963 | Chase |
| 3,109,843 A | 11/1963 | Reeder et al. |
| 3,136,815 A | 6/1964 | Reeder et al. |
| 3,243,427 A | 3/1966 | Reeder et al. |
| 3,296,249 A | 1/1967 | Bell |
| 3,299,053 A | 1/1967 | Archer et al. |
| 3,340,253 A | 9/1967 | Reeder et al. |
| 3,371,085 A | 2/1968 | Reeder et al. |
| 3,374,225 A | 3/1968 | Reeder et al. |
| 3,547,828 A | 12/1970 | Mansfield et al. |
| 3,567,710 A | 3/1971 | Fryer et al. |
| 3,609,145 A | 9/1971 | Moffett |
| 3,722,371 A | 3/1973 | Boyle |
| 3,849,341 A | 11/1974 | Lamberti |
| 3,949,072 A | 4/1976 | Tenta |
| 3,987,052 A | 10/1976 | Jackson, Jr. |
| 4,130,709 A | 12/1978 | Nagarajan |
| 4,280,957 A | 7/1981 | Walser et al. |
| 4,397,951 A | 8/1983 | Taki et al. |
| 4,440,675 A | 4/1984 | Braude |
| 4,608,278 A | 8/1986 | Frank et al. |
| 4,657,901 A | 4/1987 | Ueda et al. |
| 4,690,952 A | 9/1987 | Kagatani et al. |
| 4,748,158 A | 5/1988 | Biermann et al. |
| 4,826,689 A | 5/1989 | Violanto |
| 4,868,289 A | 9/1989 | Magnusson et al. |
| 4,921,838 A | 5/1990 | Catsimpoolas et al. |
| 4,973,465 A | 11/1990 | Bahrain et al. |
| 4,997,454 A | 3/1991 | Violante et al. |
| 5,091,188 A | 2/1992 | Haynes |
| 5,100,591 A | 3/1992 | Leclef et al. |
| 5,118,528 A | 6/1992 | Fessi et al. |
| 5,122,187 A | 6/1992 | Schwarz et al. |
| 5,145,684 A | 9/1992 | Liversidge et al. |
| 5,182,258 A | 1/1993 | Chiou |
| 5,188,837 A | 2/1993 | Domb |
| 5,192,528 A | 3/1993 | Radhakrishnan et al. |
| 5,198,420 A | 3/1993 | Donahoe et al. |
| 5,236,707 A | 8/1993 | Stewart, II |
| 5,268,461 A | 12/1993 | Shoji et al. |
| 5,308,531 A | 5/1994 | Urfer et al. |
| 5,317,010 A | 5/1994 | Pang et al. |
| 5,369,095 A | 11/1994 | Kee et al. |
| 5,457,100 A | 10/1995 | Daniel |
| 5,550,220 A | 8/1996 | Meyer et al. |
| 5,556,757 A | 9/1996 | Alstyne et al. |

(Continued)

FOREIGN PATENT DOCUMENTS

| | | |
|---|---|---|
| CN | 1303674 A | 7/2001 |
| EP | 0396777 A1 | 11/1990 |

(Continued)

OTHER PUBLICATIONS

US 5,849,884 A, 12/1998, Woiszwillo et al. (withdrawn)
U.S. Appl. No. 17/336,389, filed Jun. 2, 2021, first named inventor Steve Cartt.
Rule 36 Judgment entered Oct. 7, 2021, U.S. Court of Appeals for the Federal Circuit, *Neurelis, Inc.*, Appellant v. *Aquestive Therapeutics, Inc.*, Appellee, Appeal No. 2021-1038, affirming decision in IPR2019-00451 (U.S. Pat. No. 9,763,876).

(Continued)

*Primary Examiner* — Adam C Milligan
(74) *Attorney, Agent, or Firm* — Troutman Pepper Hamilton Sanders LLP

(57) ABSTRACT

The invention relates to pharmaceutical compositions comprising one or more benzodiazepine drugs for nasal administration, methods for producing and for using such compositions.

18 Claims, No Drawings

(56) References Cited

U.S. PATENT DOCUMENTS

| | | |
|---|---|---|
| 5,556,940 A | 9/1996 | Willick et al. |
| 5,560,932 A | 10/1996 | Bagchi et al. |
| 5,639,733 A | 6/1997 | Koike et al. |
| 5,661,130 A | 8/1997 | Meezan et al. |
| 5,662,883 A | 9/1997 | Bagchi et al. |
| 5,665,331 A | 9/1997 | Bagchi et al. |
| 5,716,642 A | 2/1998 | Bagchi et al. |
| 5,738,845 A | 4/1998 | Imakawa |
| 5,780,062 A | 7/1998 | Frank et al. |
| 5,789,375 A | 8/1998 | Mukae et al. |
| 5,795,896 A | 8/1998 | Lofroth et al. |
| 5,814,607 A | 9/1998 | Patton |
| 5,817,634 A | 10/1998 | Meezan et al. |
| 5,831,089 A | 11/1998 | Huber |
| 5,861,510 A | 1/1999 | Piscopio et al. |
| 5,863,949 A | 1/1999 | Robinson et al. |
| 5,955,425 A | 9/1999 | Morley et al. |
| 5,981,719 A | 11/1999 | Woiszwillo et al. |
| 6,004,574 A | 12/1999 | Backstrom et al. |
| 6,090,925 A | 7/2000 | Woiszwillo et al. |
| 6,143,211 A | 11/2000 | Mathiowitz et al. |
| 6,165,484 A | 12/2000 | Raad et al. |
| 6,193,985 B1 | 2/2001 | Sonne |
| 6,235,224 B1 | 5/2001 | Mathiowitz et al. |
| 6,254,854 B1 | 7/2001 | Edwards et al. |
| 6,268,053 B1 | 7/2001 | Woiszwillo et al. |
| 6,316,029 B1 | 11/2001 | Jain et al. |
| 6,316,410 B1 | 11/2001 | Barbier et al. |
| 6,375,986 B1 | 4/2002 | Ryde et al. |
| 6,395,300 B1 | 5/2002 | Straub et al. |
| 6,428,814 B1 | 8/2002 | Bosch et al. |
| 6,458,387 B1 | 10/2002 | Scott et al. |
| 6,461,591 B1 | 10/2002 | Keller et al. |
| 6,482,516 B1 | 11/2002 | Sadek et al. |
| 6,482,834 B2 | 11/2002 | Spada et al. |
| 6,495,498 B2 | 12/2002 | Niemiec et al. |
| 6,524,557 B1 | 2/2003 | Backstrom et al. |
| 6,551,578 B2 | 4/2003 | Adjei et al. |
| 6,607,784 B2 | 8/2003 | Kipp et al. |
| 6,608,073 B1 | 8/2003 | Hussain et al. |
| 6,610,271 B2 | 8/2003 | Wermeling |
| 6,616,914 B2 | 9/2003 | Ward et al. |
| 6,627,211 B1 | 9/2003 | Choi et al. |
| 6,794,357 B1 | 9/2004 | Backstrom et al. |
| 6,855,332 B2 | 2/2005 | Gizurarson et al. |
| 6,869,617 B2 | 3/2005 | Kipp et al. |
| 6,884,436 B2 | 4/2005 | Kipp et al. |
| 6,908,626 B2 | 6/2005 | Cooper et al. |
| 6,932,962 B1 | 8/2005 | Backstrom et al. |
| 6,991,785 B2 | 1/2006 | Frey et al. |
| 7,008,920 B2 | 3/2006 | Kimura et al. |
| 7,037,528 B2 | 5/2006 | Kipp et al. |
| 7,132,112 B2 | 11/2006 | Choi et al. |
| 7,220,402 B1 | 5/2007 | Andersen et al. |
| 7,425,542 B2 | 9/2008 | Maggio |
| 7,434,579 B2 | 10/2008 | Young et al. |
| 7,524,510 B2 | 4/2009 | Arnold et al. |
| 8,530,463 B2 | 9/2013 | Cartt et al. |
| 8,895,546 B2 | 11/2014 | Cartt et al. |
| 8,927,497 B2 | 1/2015 | Maggio |
| 9,192,570 B2 | 11/2015 | Wyse et al. |
| 9,642,913 B2 | 5/2017 | Maggio |
| 9,763,876 B2 | 9/2017 | Cartt et al. |
| 10,265,402 B2 | 4/2019 | Maggio |
| 2001/0042932 A1 | 11/2001 | Mathiowitz et al. |
| 2002/0110524 A1 | 8/2002 | Cowan et al. |
| 2002/0127278 A1 | 9/2002 | Kipp et al. |
| 2002/0141971 A1 | 10/2002 | Frey et al. |
| 2002/0168402 A1 | 11/2002 | Kipp et al. |
| 2003/0017203 A1 | 1/2003 | Crotts et al. |
| 2003/0031719 A1 | 2/2003 | Kipp et al. |
| 2003/0040497 A1 | 2/2003 | Teng et al. |
| 2003/0087820 A1 | 5/2003 | Young et al. |
| 2003/0095928 A1 | 5/2003 | McGurk et al. |
| 2003/0100755 A1 | 5/2003 | Sham et al. |
| 2003/0118547 A1 | 6/2003 | Vandenberg |
| 2003/0118594 A1 | 6/2003 | Nag et al. |
| 2003/0158206 A1 | 8/2003 | Billotte et al. |
| 2003/0170206 A1 | 9/2003 | Rasmussen et al. |
| 2003/0170752 A1 | 9/2003 | Andersen et al. |
| 2003/0181411 A1 | 9/2003 | Bosch et al. |
| 2004/0101482 A1 | 5/2004 | Sanders |
| 2004/0115135 A1 | 6/2004 | Quay |
| 2004/0126358 A1 | 7/2004 | Warne et al. |
| 2004/0141923 A1 | 7/2004 | Dugger et al. |
| 2004/0147473 A1 | 7/2004 | Warrell |
| 2004/0176359 A1 | 9/2004 | Wermeling |
| 2004/0209814 A1 | 10/2004 | Nauck et al. |
| 2004/0248846 A1 | 12/2004 | Quay et al. |
| 2004/0258663 A1 | 12/2004 | Quay et al. |
| 2005/0130260 A1 | 6/2005 | Linden et al. |
| 2005/0153956 A1 | 7/2005 | Merkus |
| 2005/0215475 A1 | 9/2005 | Ong et al. |
| 2005/0234101 A1 | 10/2005 | Stenkamp et al. |
| 2005/0276843 A1 | 12/2005 | Quay et al. |
| 2006/0045868 A1 | 3/2006 | Meezan et al. |
| 2006/0045869 A1 | 3/2006 | Meezan et al. |
| 2006/0046962 A1 | 3/2006 | Meezan et al. |
| 2006/0046969 A1 | 3/2006 | Maggio |
| 2006/0074025 A1 | 4/2006 | Quay et al. |
| 2006/0106227 A1 | 5/2006 | Reddy et al. |
| 2006/0147386 A1 | 7/2006 | Wermeling |
| 2006/0178290 A1 | 8/2006 | Bara |
| 2006/0183674 A1 | 8/2006 | Brand et al. |
| 2006/0198896 A1 | 9/2006 | Liversidge et al. |
| 2007/0059254 A1 | 3/2007 | Singh |
| 2007/0098805 A1 | 5/2007 | Liversidge |
| 2007/0111938 A1 | 5/2007 | Pert et al. |
| 2007/0298010 A1 | 12/2007 | Maggio |
| 2008/0070904 A1 | 3/2008 | Jamieson et al. |
| 2008/0076761 A1 | 3/2008 | Jamieson et al. |
| 2008/0194461 A1 | 8/2008 | Maggio |
| 2008/0200418 A1 | 8/2008 | Maggio |
| 2008/0248123 A1 | 10/2008 | Swanson et al. |
| 2008/0268032 A1 | 10/2008 | Maggio |
| 2008/0275030 A1 | 11/2008 | Gizurarson et al. |
| 2008/0279784 A1 | 11/2008 | Cartt et al. |
| 2008/0299079 A1 | 12/2008 | Meezan et al. |
| 2009/0004281 A1 | 1/2009 | Nghiem et al. |
| 2009/0047347 A1 | 2/2009 | Maggio |
| 2009/0130216 A1 | 5/2009 | Cartt et al. |
| 2009/0156478 A1 | 6/2009 | Lau et al. |
| 2009/0163447 A1 | 6/2009 | Maggio |
| 2009/0258865 A1 | 10/2009 | Cartt et al. |
| 2009/0297619 A1 | 12/2009 | Swanson et al. |
| 2009/0304801 A1 | 12/2009 | Liversidge et al. |
| 2009/0326193 A1 | 12/2009 | Maggio et al. |
| 2010/0068209 A1 | 3/2010 | Maggio |
| 2010/0112050 A1 | 5/2010 | Ryoo et al. |
| 2010/0160378 A1 | 6/2010 | Maggio |
| 2010/0203014 A1 | 8/2010 | Maggio |
| 2010/0203119 A1 | 8/2010 | Leane et al. |
| 2010/0209485 A1 | 8/2010 | Maggio |
| 2011/0172211 A1 | 7/2011 | Baek et al. |
| 2011/0257096 A1 | 10/2011 | Maggio |
| 2012/0196941 A1 | 8/2012 | Maggio |
| 2013/0065886 A1 | 3/2013 | Cartt et al. |
| 2013/0224300 A1 | 8/2013 | Maggio |
| 2013/0253009 A1 | 9/2013 | Maggio |
| 2014/0128479 A1 | 5/2014 | Maggio et al. |
| 2014/0170220 A1 | 6/2014 | Cartt et al. |
| 2015/0065491 A1 | 3/2015 | Cartt et al. |
| 2017/0196884 A1 | 7/2017 | Cartt et al. |
| 2020/0038320 A1 | 2/2020 | Cartt et al. |

FOREIGN PATENT DOCUMENTS

| | | |
|---|---|---|
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 0945485 A1 | 9/1999 |
| EP | 1004578 A2 | 5/2000 |
| EP | 1208863 A2 | 5/2002 |

(56) References Cited

FOREIGN PATENT DOCUMENTS

| | | | |
|---|---|---|---|
| EP | 1417972 A1 | 5/2004 |
| JP | S60208911 A | 10/1985 |
| JP | S61267528 A | 11/1986 |
| JP | H01151528 A | 6/1989 |
| JP | H05507085 A | 10/1993 |
| JP | 2003505403 A | 2/2003 |
| JP | 2005508939 A | 4/2005 |
| JP | 2007510722 A | 4/2007 |
| JP | 2009515895 A | 4/2009 |
| JP | 2011516425 A | 5/2011 |
| JP | 6883918 B2 | 6/2021 |
| WO | WO-9005719 A1 | 5/1990 |
| WO | WO-9119481 A1 | 12/1991 |
| WO | WO-9405262 A1 | 3/1994 |
| WO | WO-9500151 A1 | 1/1995 |
| WO | WO-9531217 A1 | 11/1995 |
| WO | WO-9627583 A1 | 9/1996 |
| WO | WO-9633172 A1 | 10/1996 |
| WO | WO-9714407 A1 | 4/1997 |
| WO | WO-9803516 A1 | 1/1998 |
| WO | WO-9807697 A1 | 2/1998 |
| WO | WO-9830566 A1 | 7/1998 |
| WO | WO-9833768 A1 | 8/1998 |
| WO | WO-9834915 A1 | 8/1998 |
| WO | WO-9834918 A1 | 8/1998 |
| WO | WO-9907675 A1 | 2/1999 |
| WO | WO-9929667 A1 | 6/1999 |
| WO | WO-9952889 A1 | 10/1999 |
| WO | WO-9952910 A1 | 10/1999 |
| WO | WO-2000001390 A1 | 1/2000 |
| WO | WO-0074681 A1 | 12/2000 |
| WO | WO-03004015 A1 | 1/2003 |
| WO | WO-03007978 A1 | 1/2003 |
| WO | WO-03055464 A1 | 7/2003 |
| WO | WO-2005018565 A2 | 3/2005 |
| WO | WO-2005044234 A2 | 5/2005 |
| WO | WO-2005089768 A1 | 9/2005 |
| WO | WO-2005117830 A1 | 12/2005 |
| WO | WO-2006025882 A2 | 3/2006 |
| WO | WO-2006051110 A2 | 5/2006 |
| WO | WO-2006055603 A2 | 5/2006 |
| WO | WO-2006075123 A1 | 7/2006 |
| WO | WO-2006088894 A2 | 8/2006 |
| WO | WO-2007043057 A2 | 4/2007 |
| WO | WO-2007144081 A2 | 12/2007 |
| WO | WO-2008027395 A2 | 3/2008 |
| WO | WO-2008120207 | 10/2008 |
| WO | WO-2008137960 A1 | 11/2008 |
| WO | WO-2009120933 A2 | 10/2009 |
| WO | WO-2009121039 A2 | 10/2009 |
| WO | WO-2012174158 A2 | 12/2012 |

OTHER PUBLICATIONS

Patent Owner's Preliminary Response filed May 6, 2019 in IPR2019-00449.
Decision Denying Institution of Inter Partes Review of U.S. Pat. No. 9,736,876 filed Aug. 1, 2019 in IPR2019-00449.
Petitioner's Request for Rehearing Pursuant to 37 C.F.R. 42.71(d) filed Sep. 3, 2019 in IPR2019-00449.
Decision Denying Petitioner's Request for Rehearing of Decision Denying Institution of Inter Partes Review filed Sep. 27, 2019 in IPR2019-00449.
Patent Owner's Preliminary Response filed May 6, 2019 in IPR2019-00450.
Decision Denying Institution of Inter Partes Review of U.S. Pat. No. 9,736,876 filed Aug. 1, 2019 in IPR2019-00450.
Patent Owner's Preliminary Response filed May 21, 2019 in IPR2019-00451.
Decision Instituting Inter Partes Review of U.S. Pat. No. 9,736,876 filed Aug. 13, 2019 in IPR2019-00451.
Patent Owner's Request for Rehearing filed Aug. 27, 2019 in IPR2019-00451.
Decision Denying Patent Owner's Request on Rehearing of Decision on Institution filed Sep. 27, 2019 in IPR2019-00451.
Notification of Receipt of Precedential Opinion Panel (POP) Request filed Oct. 2, 2019 in IPR2019-00451.
Patent Owner's Response to the Petition filed Nov. 5, 2019 in IPR2019-00451.
Order Denying POP Request filed Nov. 15, 2019 in IPR2019-00451.
Petitioner's Reply to Patent Owner's Response to the Petition filed Jan. 28, 2020 in IPR2019-00451.
Parties' Joint Submission of Patent Owner's Identification of New Arguments and Petitioner's Responses Thereto filed Feb. 25, 2020 in IPR2019-00451.
Patent Owner's Surreply to Patent Owner's Response filed Mar. 10, 2020 in IPR2019-00451.
Record of Oral Hearing held May 14, 2020 filed May 27, 2020 in IPR2019-00451.
Judgment Final Written Decision filed Aug. 6, 2020 in IPR2019-00451.
Patent Owner's Notice of Appeal filed Oct. 8, 2020 in IPR2019-00451.
Part 1—pp. 1-270—File History for U.S. Pat. No. 9,763,876, U.S. Appl. No. 14/527,613 (876 FH) [filed Jan. 29, 2019 as EX1002 in IPR2019-00451, IPR2019-00450, IPR2019-00449].
Part 2—pp. 271-530—File History for U.S. Pat. No. 9,763,876, U.S. Appl. No. 14/527,613 (876 FH) [filed Jan. 29, 2019 as EX1002 in IPR2019-00451, IPR2019-00450, IPR2019-00449].
Part 1—pp. 1-350—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 2—pp. 351-700—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 3—pp. 701-1050—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 4—pp. 1051-1400—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 5—pp. 1401-1750—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 6—pp. 1751-2100—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 7—pp. 2101-2450—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
Part 8—pp. 2451-2681—File History for U.S. Pat. No. 8,895,546, U.S. Appl. No. 13/495,942 (546 FH) [filed Jan. 29, 2019 as EX1004 in IPR2019-00451, IPR2019-00450, IPR2019-00449].
U.S. Appl. No. 61/497,017, filed Jun. 14, 2011 [filed as EX1005 in IPR2019-00451, IPR2019-00450, IPR2019-00449].
U.S. Appl. No. 61/570,110, filed Dec. 13, 2011 [filed as EX1006 in IPR2019-00451, IPR2019-00450, IPR2019-00449].
Part 1—pp. 1-400—File History for U.S. Appl. No. 12/413,439, filed Mar. 27, 2009 (439 FH) [filed as EX1007 in IPR2019-00451, IPR2019-00450, IPR2019-00449].
Part 2—pp. 401-800—File History for U.S. Appl. No. 12/413,439, filed Mar. 27, 2009 (439 FH) [filed as EX1007 in IPR2019-00451, IPR2019-00450, IPR2019-00449].
Part 3—pp. 801-1200—File History for U.S. Appl. No. 12/413,439, filed Mar. 27, 2009 (439 FH) [filed as EX1007 in IPR2019-00451, IPR2019-00450, IPR2019-00449].
Part 4—pp. 1201-1600—File History for U.S. Appl. No. 12/413,439, filed Mar. 27, 2009 (439 FH) [filed as EX1007 in IPR2019-00451, IPR2019-00450, IPR2019-00449].
Part 5—pp. 1601-2000—File History for U.S. Appl. No. 12/413,439, filed Mar. 27, 2009 (439 FH) [filed as EX1007 in IPR2019-00451, IPR2019-00450, IPR2019-00449].
Part 6—pp. 2001-2400—File History for U.S. Appl. No. 12/413,439, filed Mar. 27, 2009 (439 FH) [filed as EX1007 in IPR2019-00451, IPR2019-00450, IPR2019-00449].

(56) References Cited

OTHER PUBLICATIONS

Part 7—pp. 2401-2800—File History for U.S. Appl. No. 12/413,439, filed Mar. 27, 2009 (439 FH) [filed as EX1007 in IPR2019-00451, IPR2019-00450, IPR2019-00449].
Part 8—pp. 2801-3200—File History for U.S. Appl. No. 12/413,439, filed Mar. 27, 2009 (439 FH) [filed as EX1007 in IPR2019-00451, IPR2019-00450, IPR2019-00449].
Part 9—pp. 3201-3488—File History for U.S. Appl. No. 12/413,439, filed Mar. 27, 2009 (439 FH) [filed as EX1007 in IPR2019-00451, IPR2019-00450, IPR2019-00449].
U.S. Appl. No. 61/040,558, filed Mar. 28, 2008 [filed as EX1008 in IPR2019-00451, IPR2019-00450, IPR2019-00449].
Ritschel, Handbook of Basic Pharmacokinetics, Chapter 36 (Bioavailability and Bioequivalence). Drug Intelligence Publications, Illinois (1992) [filed as EX1023 in IPR2019-00451, IPR2019-00450, IPR2019-00449].
Osborne et al., Skin Penetration Enhancers Cited in the Technical Literature, Pharmaceutical Technology (Nov. 1997) [filed as EX1024 in IPR2019-00451, IPR2019-00450, IPR2019-00449].
Lindhardt et al., Electroencephalographic effects and serum concentrations after intranasal and intravenous administration of diazepam to healthy volunteers. Blackwell Science Ltd Br J Clin Pharmacol, 52 (2001): 521-527 [filed as EX1025 in IPR2019-00451, IPR2019-00450, IPR2019-00449].
Kibbe, editor, Handbook of Pharmaceutical Excipients. Third Edition, American Pharmaceutical Association, Washington DC (2000) [filed as EX1026 in IPR2019-00451, IPR2019-00450, IPR2019-00449].
Illum, Nasal drug delivery-possibilities, problems and solutions. Journal of Controlled Release 87 (2003): 187-198 [filed as EX1027 in IPR2019-00451, IPR2019-00450, IPR2019-00449].
Ivaturi et al., Pharmacokinetics and tolerability of intranasal diazepam and midazolam in healthy adult volunteers. Acta Neurol Scand., 120(5) (Nov. 2009): 353-357. doi: 10.1111/j.1600-0404.2009.01170.x. Epub May 14, 2009 [filed as EX1028 in IPR2019-00451, IPR2019-00450, IPR2019-00449].
O'Dell et al., School nurses' experience with administration of rectal diazepam gel for seizures. J Sch Nurs., 23(3) (Jun. 2007): 166-169 [filed as EX1029 in IPR2019-00451, IPR2019-00450, IPR2019-00449].
Gizurarson et al., Intranasal Administration of Diazepam Aiming at the Treatment of Acute Seizures: Clinical Trials in Healthy Volunteers. Biological and Pharmaceutical Bulletin, vol. 22 Issue 4 (1999): 425-427 [filed as EX1030 in IPR2019-00451, IPR2019-00450, IPR2019-00449].
Rowe et al., editors, Handbook of Pharmaceutical Excipients, Fourth Edition (2003), Monographs, American Pharmaceutical Association, Washington DC (2003), pp. 13-15, 27-29, 53-55, 257-259, 414-416, 454-459, 521-523, 535-537, 659-660 [filed as EX1031 in IPR2019-00451, IPR2019-00450, IPR2019-00449].
Edman et al., Microspheres as a nasal delivery system for peptide drugs. Journal of Controlled Release, 21 (1992): 165-172 [filed as EX1032 in IPR2019-00451, IPR2019-00450, IPR2019-00449].
French et al., Pharmaceutical Standards and Specifications for Bulk Drugs and Solid Oral Dosage Forms. Journal of Pharmaceutical Sciences, 56(12) (Dec. 1967): 1622-1641 [filed as EX1033 in IPR2019-00451, IPR2019-00450, IPR2019-00449].
Edman et al., (D) Routes of Delivery: Case Studies—(1) Nasal delivery of peptide drugs, Advanced Drug Delivery Reviews, 8 (1992): 165-177 [filed as EX1034 in IPR2019-00451, IPR2019-00450, IPR2019-00449].
Davis, Delivery of peptide and non-peptide drugs through the respiratory tract. Pharmaceutical Science & Technology Today, 2(11) (Nov. 1999): 450-456 [filed as EX1035 in IPR2019-00451, IPR2019-00450, IPR2019-00449].
Deshmukh et al., Lorazepam in the Treatment of Refractory Neonatal Seizures. Am J Dis Child., 140(10) (1986): 1042-1044 [filed as EX1036 in IPR2019-00451, IPR2019-00450, IPR2019-00449].
Colombo, Mucosal Drug Delivery, Nasal. Encyclopedia of Controlled Drug Delivery (Mathiowitz, editor), John Wiley & Sons, vol. 2 (1999): 592-605 [filed as EX1037 in IPR2019-00451, IPR2019-00450, IPR2019-00449].
Behl et al., Effects of physicochemical properties and other factors on systemic nasal drug delivery. Advanced Drug Delivery Reviews 29 (1998) 89: 116 [filed as EX1039 in IPR2019-00451, IPR2019-00450, IPR2019-00449].
Part 1—pp. 1-250—File History for EP 128 01372.9, based on WO 2012/174158 and PCT/US2012/042311 [filed Jan. 29, 2019 as EX1040 in IPR2019-00541, IPR2019-00450, IPR2019-00449].
Part 2—pp. 251-500—File History for EP 128 01372.9, based on WO 2012/174158 and PCT/US2012/042311 [filed Jan. 29, 2019 as EX1040 in IPR2019-00541, IPR2019-00450, IPR2019-00449].
Part 3—pp. 501-662—File History for EP 128 01372.9, based on WO 2012/174158 and PCT/US2012/042311 [filed Jan. 29, 2019 as EX1040 in IPR2019-00541, IPR2019-00450, IPR2019-00449].
Declaration of Dr. Nicholas A. Peppas executed Dec. 6, 2018 [filed as EX1041 in IPR2019-00449].
Declaration of Dr. Nicholas A. Peppas executed Dec. 6, 2018 [filed as EX1041 in IPR2019-00450].
Declaration of Dr. Nicholas A. Peppas executed Dec. 6, 2018 [filed as EX1041 in IPR2019-00451].
PDR 54th Edition 2000, Diastat (diazepam rectal gel); Miacalcin (Calcitonin Nasal Spray); Valium (diazepam injection), Physicians' Desk Reference [filed as EX1042 in IPR2019-00451, IPR2019-00450, IPR2019-00449].
Knoester et al., Pharmacokinetics and pharmacodynamics of midazolam administered as a concentrated intranasal spray. A study in healthy volunteers. Br J Clin Pharmacol, 53(5) (May 2002): 501-507 [filed as EX1043 in IPR2019-00451, IPR2019-00450, IPR2019-00449].
USP NF 2003, The United States Pharmacopeia, The National Formulary, United States Pharmacopeial Convention, Inc., (1088) in Vitro and in Vivo Evaluation, p. 2334-2339 [filed as EX1044 in IPR2019-00451, IPR2019-00450, IPR2019-00449].
Maitani et al., Design of ocular/lacrimal and nasal systems through analysis of drug administration and absorption. Journal of Controlled Release, 49(2-3) (Dec. 15, 1997): 185-192 [filed as EX1045 in IPR2019-00451, IPR2019-00450, IPR2019-00449].
U.S. Appl. No. 61/040,281, filed Mar. 28, 2008 [filed as EX1046 in IPR2019-00451, IPR2019-00450, IPR2019-00449].
Assignment of U.S. Appl. No. 12/933,701 recorded at Reel:Frame 025034:0531 on Sep. 23, 2010 [filed as EX1047 in IPR2019-00451, IPR2019-00450, IPR2019-00449].
Assignment of U.S. Appl. No. 12/116,842 recorded at Reel:Frame 027955:0600 on Mar. 29, 2012 [filed Jan. 29, 2019 as EX1049 in IPR2019-00451].
Table of Various Diazepam Solutions Described in or Modified From Sonne's Example 11 [filed as EX1050 in IPR2019-00451, IPR2019-00450].
U.S. Appl. No. 60/632,038, filed Nov. 30, 2004 [filed as EX1065 in IPR2019-00451, IPR2019-00450].
Florida Regional Common EMS Protocols Field Guide, Jones and Barlett Publishers, MA (2005) [filed as EX1069 in IPR2019-00451].
Nayzilam Product Label and Instructions for Use Revised May 2019 [filed as EX1072 in IPR2019-00451].
Hardman, et al., Editors, Goodman & Gilman's, The Pharmacological Basis of Therapeutics, 10th Edition (2001) [filed as EX1074 in IPR2019-00451].
Budavari, et al., Editors, The Merck Index, 12th Edition (1996), p. xiii-xiv, xv-xviii, 508, 189, 641-642, 1712 [filed as EX1076 in IPR2019-00451].
Ritchel, W.A. et al., Handbook of Basic Pharmocokinetics Including Clinical Applications, 6th Edition, 2004 [filed as EX1077 in IPR2019-00451].
USP/NF 2003, The Official Compendia of Standards, Ethanol, 2002, Alcohol, p. 59-60 [filed as EX1078 in IPR2019-00451].
VALIUM Tablet Label, Roche, Jan. 2008 [filed as EX1080 in IPR2019-00451].
Drug Prices from Internet (Accessed Jan. 24, 2020) [filed as EX1081 in IPR2019-00451].

(56) References Cited

OTHER PUBLICATIONS

Chien, Y.W et al., "Nasal Systemic Drug Delivery", Chapter 1, Anatomy and Physiology of the Nose, Drugs and the Pharmaceutical Sciences, vol. 39, Marcel Decker, 1989 [filed as EX1082 in IPR2019-00451].
Lowenstein DH, Alldredge BK. Status epilepticus. N Eng J Med 1998; 338: 970-976 [filed as EX1101 in IPR2019-00451].
Lowenstein DH, Bieck T, Macdonald RL. It's time to revise the definition of status epilepticus. Epilepsia 1999; 40: 120-122 [filed as EX1102 in IPR2019-00451].
Wang HC, Chang WN, Chang HW et al. Factors predictive of outcome in posttraumatic seizures. J Trauma 2008; 64: 883-888 [filed as EX1103 in IPR2019-00451].
Stavem K, BJornaes H, Langmoen IA. Long-term seizures and quality of life after epilepsy surgery compared with matched controls. Neurosurgery 2008; 62: 326-334 [filed as EX1104 in IPR2019-00451].
Logroscino G, Hessdorffer DC, Cascino G et al. Time trends in incidence, mortality, and case-fatality after first episode of status epilepticus. Epilepsia 2001; 42: 1031-1035 [filed as EX1105 in IPR2019-00451].
Feen ES, Bershad EM, Suarez JI. Status Epilepticus. South Med J 2008; 101: 400-406 [filed as EX1106 in IPR2019-00451].
Pang T, Hirsch L. Treatment of convulsive and nonconvulsive status epilepticus. Cur Treat Options Neurol 2005; 7: 247-259 [filed as EX1107 in IPR2019-00451].
Smith B. Treatment of status epilepticus. Neurol Clin 2001; 19: 347-369 [filed as EX1108 in IPR2019-00451].
Ericksson K, Kalviainen R. Pharmacologic management of convulsive status epilepticus in childhood. Expert Rev Neurotherapeutics 2005; 5: 777-783 [filed as EX1109 in IPR2019-00451].
Wolfe T, Macfarlane T. Intranasal midazolam therapy for pediatric status epilepticus. Am J Emerg Med 2006; 24: 343-346 [filed as EX1110 in IPR2019-00451].
Meierkord H, Engelsen B, Goeke K et al. EFNS guideline on the management of status epilepticus. Eur J Neurol 2006; 13: 445-450 [filed as EX1111 in IPR2019-00451].
Prasad K, Krishman P, Al-Roomi K et al., Anticonvulsant therapy for status epilepticus. Br J Clin Pharmacol 2007; 63: 640-647 [filed as EX1112 in IPR2019-00451].
Illum L. Nasal Clearance in Health and Disease. J Aerosol Med 2006; 19: 92-99 [filed as EX1113 in IPR2019-00451].
Merkus P, Ebbens FA, Muller B, Fokkens WJ. Influence of anatomy and head position on intranasal drug deposition. Eur Arch Otorhinolaryngol 2006; 263: 827-832 [filed as EX1114 in IPR2019-00451].
Illum L. Transport of drugs from the nasal cavity to the central nervous system. Eur J Pharm Sci 2000; 11: 1-18 [filed as EX1115 in IPR2019-00451].
Illum L. Is nose to brain transport of drugs a reality?. JPP 2004; 56: 3-17 [filed as EX1116 in IPR2019-00451].
Merkus F, van den Berg MP. Can nasal drug delivery bypass the blood-brain barrier? Questioning the direct transport theory. Drugs 2007; 8: 133-144 [filed as EX1117 in IPR2019-00451].
Constantino HR, Illlum L, Brandt G et al., Intranasal delivery: Physicochemical and therapeutic aspects, Intl J Pharmaceutics 2007; 337: 1-24 [filed as EX1118 in IPR2019-00451].
Davis GA, Rudy AC, Archer SA, Wermeling DP, McNamara PJ. Effect of fluticasone propionate nasal spray on bioavailability of hydromorphone hydrochloride in patients with allergic rhinitis. Pharmacotherapy 2004; 24: 26-32 [filed as EX1119 in IPR2019-00451].
Davis GA, Rudy AC, Archer SM, Wermeling DP, McNamara PJ., Bioavailability and pharmacokinetics of intranasal hydromorphone in patients experiencing vasomotor rhinitis. Clin Drug Invest 2004; 24: 1-7 [filed as EX1120 in IPR2019-00451].
Holsti M, Sill B, Firth S et al., Prehospital intranasal midazolam for the treatment of pediatric seizures. Ped Emerg Care 2007; 23: 148-153 [filed as EX1121 in IPR2019-00451].
Rudy AC, Coda BA, Archer SM, Wermeling DP. A multiple dose phase 1 study of intranasal hydromorphone hydrochloride in healthy volunteers. Anesth Analg 2004; 99: 1379-1386 [filed as EX1122 in IPR2019-00451].
Loftsson T, Gudmundsdottir H, Sigurjonsdottir JF et al. Cyclodextrin solubilization of benzodiazepines: formulation of midazolam nasal spray. Int J Pharm 2001; 212: 29-40 [filed as EX1125 in IPR2019-00451].
Gudmundsdottir H, Sigurjonsdottir JF, Masson M et al., Intranasal administration of midazolam in a cyclodextrin based formulation: bioavailability and clinical evaluation in humans. Pharmazie 2001; 56: 963-966 [filed as EX1127 in IPR2019-00451].
Dale O., Nilsen T., Loftsson T. Intranasal midazolam: a comparison of two delivery devices in human volunteers. J Pharmacy Pharmacol 2006; 58: 1311-1318 [filed as EX1128 in IPR2019-00451].
Burstein AH, Modica R, Hatton M et al. Pharmacokinetics and pharmacodynamics of midazolam after intranasal administration. J Clin Pharmacol 1997; 37: 711-718 [filed as EX1129 in IPR2019-00451].
Schols-Hendriks MWG, Lohman JJHM, Janknegt R et al. Absorption of clonazepam after intranasal and buccal administration. Br J Clin Pharmacol, 1995; 39: 449-451 [filed as EX1131 in IPR2019-00451].
Wermeling DP, Miller JL, Archer SM et al. Bioavailability and pharmacokinetics of lorazepam after intranasal, intravenous, and intramuscular administration. J Clin Pharmacol, 2001; 41: 1225-1231 [filed as EX1134 in IPR2019-00451].
Greenblatt D, Gan L, Harmatz et al. Pharmacokinetics and pharmacodynamics of single-dose triazolam: EEG compared with digital symbol substitution test. Br J Clin Pharmacol 2005; 60: 244-248 [filed as EX1135 in IPR2019-00451].
O'Regan M, Brown J, Clarke M., Nasal rather than rectal benzodiazepines in the management of acute childhood seizures. Develop Med and Child Neurol 1996; 38: 1037-1045 [filed as EX1136 in IPR2019-00451].
Mittal P, Manohar R, Rawat A. Comparative study of intranasal midazolam and intravenous diazepam sedation for procedures and seizures. Ind J Pediatrics (2006)73: 975-978 [filed as EX1137 in IPR2019-00451].
Mahmoudian T, Zadeh M. Comparison of intranasal midazolam with intravenous diazepam for treating acute seizures in children. Epilepsy and Behavior 2004; 5: 253-255 [filed as EX1138 in IPR2019-00451].
Lahat E, Goldman M, Barr J et al. Comparison of intranasal midazolam with intravenous diazepam in treating febrile seizures in children: prospective randomized study. BMJ 2000; 321: 83-87 [filed as EX1139 in IPR2019-00451].
Bhattacharyya M, Kalra V, Gulati S. Intranasal midazolam vs rectal diazepam in acute childhood seizures. Pediatric Neurology 2006; 34: 355-359 [filed as EX1140 in IPR2019-00451].
Wilson, M.T., S. Macleod, and M.E. O'Regan, Nasal/buccal midazolam use in the community. Arch Dis Child, 2004. 89(1): p. 50-51 [filed as EX1141 in IPR2019-00451].
Harbord, M.G. et al., Use of intranasal midazolam to treat acute seizures in paediatric community settings. J Paediatr Child Health, 2004. 40(9-10): p. 556-558 [filed as EX1142 in IPR2019-00451].
Jeannet, P.Y. et al., Home and hospital treatment of acute seizures in children with nasal midazolam. Eur J Paediatr Neurol, 1999. 3(2): p. 73-77 [filed as EX1143 in IPR2019-00451].
Ahmad S, Ellis J, Kamwendo H et al. Efficacy and safety of intranasal lorazepam versus intramuscular paraldehyde for protracted convulsions in children: an open label trial. Lancet 2006; 367: 1591-1597 [filed as EX1144 in IPR2019-00451].
Wolfe T, Bernstone T, Intranasal Drug Delivery: An Alternative to Intravenous Administration in Selected Emergency Cases, J Emerg Nurs. Apr. 2004;30(2): 141-7 [filed as EX1145 in IPR2019-00451].
FDA GUI Final, Determining Whether to Submit an ANDA or a 505(b)(2) Application, Published May 2019, https://www.fda.gov/media/123567/download [filed as EX1146 in IPR2019-00451].
CDER Sep. 19, 2019—Abbreviated Approval Products:505(b)(2) or ANDA at https://www.fda.gov/drugs/cder-small-business-industry-

(56) References Cited

OTHER PUBLICATIONS assistance-sbia/abbreviated-approval-pathways-drug-product-505b2-or-anda-september-19-2019-issue (2019) [filed as EX1147 in IPR2019-00451].

FDA Guidance for Industry (1999), Applications Covered by Section 505(b)(2), https://www.fda.gov/media/72419/download [filed as EX1148 in IPR2019-00451].

Transcript of the Jan. 14, 2020 deposition of Dr. Gizararson [filed as EX1149 in IPR2019-00451].

Declaration of Daniel P. Wermeling, Pharm.D. executed Jan. 27, 2020 [filed as EX1150 in IPR2019-00451].

Wermeling, D.P., Intranasal delivery of antiepileptic medications for treatment of seizures, Neurotherapeutics, Apr. 2009, vol. 6, Issue 2, pp. 352-358 [filed as EX1151 in IPR2019-00451].

Declaration of Michael I. Chakansky executed Feb. 19, 2020 [filed as EX1152 in IPR2019-00451].

Epilepsy Fast Facts, CDC (Center for Disease Control and Preventions), CDC 24/7: Saving Lives, Protection People, Apr. 9, 2019, pp. 1-2, available at https://www.cdc.gov/epilepsy/about/fast-facts.htm7CDC_AA_refVal=https%3A%2F%2Fwww.cdc.gov%2Fepilepsy%2Fbasics%2Ffast-facts.htm [filed as EX2001 in IPR2019-00451, IPR2019-00450, IPR2019-00449].

Food & Drug Administration, Grant Fast Track (IND 112621; NRL-1 (diazepam intranasal solution)) (Dec. 27, 2016) [filed as EX2002 in IPR2019-00451, IPR2019-00450, IPR2019-00449].

Lewine, M.D., Howard, Quick Injection Helps Stop Epileptic Seizures, Harvard Health Blog (Feb. 23, 2012), available at https://www.health.harvard.edu/blog/quick-injection-helps-stop-epileptic-seizures-201202234319/print/ [filed as EX2003 in IPR2019-00451, IPR2019-00450, IPR2019-00449].

"Managing Epilepsy Well Network and Selected Self-Management Programs; Putting Collective Wisdom to Work for People with Epilepsy," Prevention Research Centers (PRC), CDC (Nov. 2016) [filed as EX2004 in IPR2019-00451, IPR2019-00450, IPR2019-00449].

Fiest, K.M. et al., "Prevalence and Incidence of Epilepsy, a Systematic Review and Meta-Analysis of International Studies," Neurology 88, Jan. 17, 2017, pp. 296-303 [filed as EX2005 in IPR2019-00451, IPR2019-00450, IPR2019-00449].

SIGMA Chemical Company Catalog (1988) [filed as EX2006 in IPR2019-00451].

Bechgaard E. et al., "Solubilization of Various Benzodiazepines for Intranasal Administration, a Pilot Study," Pharmaceutical Development and Technology 2: 293-296 (1997) [filed as EX2007 in IPR2019-00451].

Hussain A. et al. "Nasal Absorption of Propranolol in Humans," Journal of Pharmaceutical Sciences 69: 1240 (1980) [filed as EX2008 in IPR2019-00451].

Lau S. and J. Slattery, "Absorption of Diazepam and Lorazepam Following Intranasal Administration," International Journal of Pharmaceutics, 54: 171-174 (1989) [filed as EX2009 in IPR2019-00451].

Schols-Hendriks M. et al., "Absorption of Clonazepam After Intranasal and Buccal Administration," British Journal of Clinical Pharmacology 39: 449-451 (1995) [filed as EX2010 in IPR2019-00451].

Dr. Nicholas Peppas Deposition Transcript, Oct. 24, 2019 [filed as EX2011 in IPR2019-00451].

Declaration of Dr. Sveinbjorn Gizurarson, Ph.D. executed Nov. 4, 2019 [filed as EX2012 in IPR2019-00451].

Riss J. et al., "Benzodiazepines in Epilepsy: Pharmacology and Pharmacokinetics," Acta Neurologica Scandinavica 118: 69-86 (2008) [filed as EX2013 in IPR2019-00451].

Cole C. et al., "Community Survey of Carer's: Individual Epilepsy Guidelines (IEG) for Rescue Medication," Seizure 18: 220-224 (2009) [filed as EX2015 in IPR2019-00451].

Terry D. et al., "Acceptance of the Use of Diazepam Rectal Gel in School and Day Care Settings," Journal of Child Neurology 22: 1135-1138 (2007) [filed as EX2016 in IPR2019-00451].

DIASTAT Label (2005) [filed as EX2017 in IPR2019-00451].

"UCB announces NAYZILAM (midazolam) nasal spray now approved by FDA to treat intermittent, stereotypic episodes of frequent seizure activity in people living with epilepsy in the U.S.," UCB Press Release (2019) (Accessed Oct. 31, 2019) [filed as EX2018 in IPR2019-00451].

French J. and T. Pedley, "Initial Management of Epilepsy," New England Journal of Medicine 359: 166-176 (2008) [filed as EX2019 in IPR2019-00451].

Corbo G. et al., "Measurement of Nasal Mucociliary Clearance," Archives of Disease in Childhood 64: 546-550 (1989) [filed as EX2020 in IPR2019-00451].

"How does the nose work? The nasal mucosa," https://www.fitonasal2act.com/how-does-the-nose-work/the-nasal-mucosa/ (Accessed Nov. 5, 2019) [filed as EX2021 in IPR2019-00451].

Mygind N. "Nasal Allergy," 9 (Blackwell Scientific Publications, 1979) [filed as EX2022 in IPR2019-00451].

"Neurelis Files New Drug Application With the FDA for Valtoco (Diazepam Nasal Spray), an Investigational Treatment for Pediatric, Adolescent and Adult Epilepsy Patients," (2018) (Accessed Nov. 1, 2019) [filed as EX2023 in IPR2019-00451].

"Neurelis Receives FDA Orphan Drug Designation for NRL-1 in the Treatment of Acute Repetitive Seizures," https://www.neurelis.com/neurelis-news/fda-orphan-drug-designation (2015) (Accessed Nov. 1, 2019) [filed as EX2024 in IPR2019-00451].

Affidavit of Robert Cleary executed Nov. 21, 2019 [filed as EX2025 in IPR2019-00451].

Affidavit of Ronald Figueroa executed Nov. 21, 2019 [filed as EX2026 in IPR2019-00451].

Transcript of Telephone Conference on Feb. 11, 2020 [filed as EX2027 in IPR2019-00451].

"Intranasal Technology, Inc. Licenses Aegis Therapeutics' Intravail Drug Delivery Technology" (Business Wire) (Apr. 13, 2005) [filed as EX2028 in IPR2019-00451].

Handbook of Pharmaceutical Excipients (Pharmaceutical Press and American Pharmacists Association, Publishers) (Fifth Edition, 2006) [filed as EX2029 in IPR2019-00451].

Daniel P. Wermeling Deposition Transcript, Feb. 26, 2020 [filed as EX2031 in IPR2019-00451].

Email sent Sep. 30, 2019 requesting Precedential Opinion Panel review [filed as EX3001 in IPR2019-00451].

Appellant Neurelis Inc.'s Opening Brief filed Feb. 2, 2021 in Appeal Case No. 21-1038 (Court of Appeals for the Federal Circuit).

Corrected Brief for Appellee Aquestive Therapeutics, Inc. filed Mar. 31, 2021 in Appeal Case No. 21-1038 (Court of Appeals for the Federal Circuit).

Appellant Neurelis Inc.'s Reply Brief filed May 3, 2021 in Appeal Case No. 21-1038 (Court of Appeals for the Federal Circuit).

Notice Forwarding Certified List filed Nov. 18, 2020 in Appeal Case No. 21-1038 (Court of Appeals for the Federal Circuit).

U.S. Appl. No. 14/948,081 Office Action dated Apr. 10, 2019.
U.S. Appl. No. 15/470,498 Office Action dated Sep. 12, 2019.
U.S. Appl. No. 15/470,498 Office Action dated May 5, 2020.
U.S. Appl. No. 16/594,897 Office Action dated Apr. 9, 2021.
U.S. Appl. No. 60/148,464, filed Aug. 12, 1999, Noe.
U.S. Appl. No. 15/955,397 Office Action dated Oct. 7, 2019.
U.S. Appl. No. 15/955,397 Office Action dated Mar. 20, 2020.

Sun et al. "Nasal spray for curing status epilepticdus (SE) ad eples, comprises alprazolam and carriers" Thompson Scientific Database WPI, Section Ch., week 200164 Abstract.

Chinese Serial No. 201710940124.1 Office Action dated Nov. 25, 2019.

EP 08747813.7 Office Action dated Jun. 24, 2011.

EP 12801372.9 Summons to Attend Oral Proceedings with Annex dated May 16, 2017.

Japanese Serial No. 2019-083274 Office Action dated Mar. 25, 2020.

Japanese Serial No. 2019-083274 Office Action dated Nov. 18, 2020.

Chinese Serial No. 201710940124.1 Office Action dated Sep. 28, 2020.

Wang, Xiaobo, "Drug Delivery and Release System," China Medical Science and Technology Press, pp. 356-357, Aug. 2007.

EP 18171484.1 Office Action dated Apr. 6, 2020.

(56) References Cited

OTHER PUBLICATIONS

EP 18171484.1 Office Action dated May 17, 2021.
Ahsan et al., Effects of the permeability enhancers, tetradecylmaltoside and dimethyl-β-cyclodextrin, on insulin movement across human bronchial epithelial cells. European Journal of Pharmaceutical. Sciences, 20.1 (2003): 27-34.
Ahsan et al., Sucrose cocoate, a component of cosmetic preparations enhances nasal and ocular peptide absorption. Int J Pharm., 251.1-2 (2003): 195-203.
Albert et al., Pharmacokinetics of diphenhydramine in man. J. Pharmacokinet, Biopharm., 3.3 (1975): 159-170.
Arnold et al., Correlation of tetradecylmaltoside induced increases in nasal peptide drug delivery with morphological changes in nasal epithelial cells. J. Pharm. Sci., 93.9 (2004): 2205-2213.
Australian Serial No. 2009228093 First exam report dated Jul. 19, 2013.
Beam et al., Blood, Brain, Cerebrospinal Fluid Concentrations of Several Antibiotics in Rabbits with Intact and Inflamed Meninges. Antimicrobal Agents and Chemotherapy, (1977): 710-716.
Berrocoso et al., Opiates as Antidepressants. Curr Pharma Design, 15 (2009): 1612-1622.
Bhairi., A guide to the properties and uses of detergents in biological systems. Calbiochem., (2001): 1-42.
Birkett et al., Bioavailability and First Pass Clearance. Australian Prescriber, 14 (1991): 14-16.
Birkett et al., How Drugs are Cleared by the Liver. Australian Prescriber, 13.4 (1990): 88-89.
Brown et al., Affinity Purification of a Somatostatin Receptor-G-Protein Complex demonstrates Specificity in Receptor-G-Protein Coupling. J. Biol. Chem. 268.9 (1993): 6668-6676.
Canadian Patent Application No. 2756690 Examiner's Report dated Oct. 20, 2015.
Canadian Serial No. 2756690 Office Action dated Feb. 19, 2015.
Canadian Serial No. 2,723,470 Office Action dated Jun. 7, 2012.
Castro et al., Ecologically safe alkyl glucoside-based gemini surfactants. Arkivoc, xii (2005): 253-267.
Chavanpatil et al., Nasal drug delivery of sumatriptan succinate. Pharmazie., 60.5 (2005): 347-349.
Chen et al., Peptide Drug Permeation Enhancement by Select Classes of Lipids. Presented ath the 45th American Society of Cell Biology, S.F., CA, Dec. 10-14, 2005; 1 page.
Chen-Quay et al., Identification of tight junction modulating lipids. J. Pharm. Sci., 98.2 (2009): 606-619.
Chinese Patent Application No. 201280039077.9 Second Office Action dated Aug. 11, 2015.
Chinese Serial No. 200980157305.0 Office Action dated Jan. 28, 2013.
Chinese Serial No. 201280039077.9 Office Action dated Dec. 26, 2014.
Chinese Serial No. 201280039077.9 Office Action dated Nov. 21, 2016.
Chinese Serial No. 201280039077.9 Reexamination Notification dated Jun. 29, 2017.
Chinese Serial No. 201280039077.9 Third Office Action dated Mar. 17, 2016.
Chiou et al., Improvement of Systemic Absorption of Insulin Through Eyes with Absorption Enhancers. Journal of Pharmaceutical Sciences, 78.10 (1989): 815-818.
Chiou et al., Systemic Delivery of Insulin Through Eyes to Lower the Glucose Concentration. Journal of Ocular Pharmacology, 5.1 (1989): 81-91.
Christensen et al., Once-weekly GLP-1 agonists: How do they differ from exenatide and liraglutide? Curr. Diab. Rep., 10.2 (2010): 124-32.
Davis et al., Absorption enhancers for nasal drug delivery. Clin. Pharmacokine., 42.13 (2003): 1107-28.
De Vry et al., Effects of selected serotonin 5-HT(1) and 5-HT(2) receptor agonists on feeding behavior: possible mechanisms of action. Neurosci. Biobehav. Rev., 24.3 (2000): 341-353.

Definition of Encephalin, 1 page. Downloaded on Sep. 13, 2012 from:http://medical-dictionary.thefreedictionary.com/p/encephalin.
Definition of pilus, Merriam-Webster Medical Dictionary, http://www.nnerriam-webster_com/medical/pilus, accessed online on May 28, 2013.
Definition of villus, Merriam-Webster Medical Dictionary, Downloaded on May 28, 2013 from http://www.merriam-webster.com/medical/villus.
Drewe et al., Enteral absorption of octreotide: absorption enhancement by polyoxyethylene-24-cholesterol ether. Br. J. Pharmacol., 108.2 (1993): 298-303.
Duquesnoy et al., Comparative clinical pharmacokinetics of single doses of sumatriptan following subcutaneous, oral, rectal and intranasal administration. Eur. J. Pharm. Sci., 6.2 (1998): 99-104.
Edwards., GLP-1: target for a new class of antidiabetic agents?. J.R. Soc. Med., 97.6 (2004): 270-274.
Eley et al., In vitro assessment of alkylglycosides as permeability enhancers. AAPS PharmsciTech., article 19, 2.3 (2001): 1-7.
EP08747813 Supplementary Search Report dated Jun. 2, 2010.
EP09723906.5 Extended European search report dated Jun. 3, 2013.
EP09835809 European Search Report dated Nov. 13, 2012.
EP11835002 Supplementary European Search Report dated Jul. 7, 2015.
EP12801372.9 Communication from the Examining Division dated Jul. 5, 2016.
EP12801372.9 Extended European Search Report dated Mar. 26, 2015.
Fetih et al., Improvement of absorption enhancing effects of n-dodecyl-13-D-maltopyranoside by its colon-specific delivery using chitosan capsules. Int. J. Pharmaceutics, 293 (2005): 127-135.
Fix. Oral controlled release technology for peptides: status and future prospects. Pharm Res. 13(12):1760-1764 (1996).
Fricker et al., Permeation enhancement of octreotide by specific bile salts in rats and human subjects: in vitro, in vivo correlations. Br. J. Pharmacol., 117.1 (1996): 217-23.
Gordon et al., Nasal Absorption of Insulin: Enhancement by Hydrophobic Bile Salts. Proceedings of the National Academy of Sciences of the United States of America, 82 (1985): 7419-7423.
Hathcox et al., Inhibitory effects of sucrose fatty acid esters, alone and in combination with ethylenediaminetetraacetic acid and other organic acids, on viability of *Escherichia coli* 0157:H7. Food Microbiology, 13.3 (1996): 213-225.
Hovgaard et al., Insulin Stabilization and GI Absorption, Journal of Controlled Release, 19.1-3 (1992): 99-108.
Hovgaard et al., Stabilization of insulin by alkylmaltosides. A. Spectroscopic evaluation. International Journal of Pharmaceutics, 132.1-2 (1996): 107-113.
Hovgaard et al., Stabilization of Insulin by Alkylmaltosides. B. Oral Absorption in Vivo in Rats. International Journal of Pharmaceutics, 132 (1996): 115-121.
Hovgaard, Lars., et al. Insulin Stabilization and Gastrointestinal Absorption; dissertation, Dept. Pharmaceutics, Univ. Utah, Aug. 1991.
Hussain et al., Absorption enhancers in pulmonary protein delivery. J Control Release. Jan. 8, 2004;94(1):15-24.
Illum et al., Nasal drug delivery—Recent developments and future prospects. J. Controlled AH Release 161.2 (2012): 254-263.
Japanese Serial No. 2010-507633 Decision of refusal dated Jul. 9, 2013.
Japanese Serial No. 2010-507633 Office Action dated Oct. 23, 2012.
Japanese Serial No. 2014-515967 Office Action dated Apr. 24, 2017.
Japanese Serial No. 2014-515967 Office Action dated Mar. 30, 2016.
Japanese Serial No. 2014-515967 Office Action dated Nov. 28, 2016.
Japanese Serial No. 2017-185485 Office Action dated Jul. 2, 2018.
Katzung, B., Basic and Clinical Pharmacology, 7th Edition, Appleton & Lange: Stamford, Connecticut, 1998, 34-49.
Kissel et al., Tolerability and absorption enhancement of intranasally administered octreotide by sodium taurodihydrofusidate in healthy subjects. Pharm Res., 9.1 (1992): 52-57.

(56) References Cited

OTHER PUBLICATIONS

Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.

Knudsen, L. B., Glucagon-like Peptide-1: The Basis of a New Class of Treatment for Type 2 Diabetes. J. Med. Chem., 47 (2004): 4128-4134.

Lacy et al., Drug Information Handbook. 7th Edition 1999-2000, Lexi-Comp Inc., (1999): 163-164.

Lahat et al., Intranasal midazolam for childhood seizures. The Lancet, 352.9128 (1998): 620.

Lehninger et al., Principles of Biochemistry with an Extended Discussion of Oxygen-Binding Proteins, Worth Publishers, Inc., 1982: 150-151.

Liu et al., Interaction between chitosan and alkyl P-D-glucopyranoside and its effect on their antimicrobial activity. Carbohydrate Polymers, 56 (2004): 243-250.

MAA., Biopharmaceutical powders: particle formation and formulation considerations. Curr. Pharm. Biotechnol., 1.3 (2000): 283-302.

Material Safety Data Sheet for Anatrace, Inc., product n-Dodecyl-6-D-Maltopyranoside, Anagrade, Dated: Jan. 25, 1994 and Revised: Jul. 15, 2004, http://media.affymetrix.com/suoport/technical/anatrace/msds/D310.pdf, accessed online on Dec. 13, 2012.

Mathew., Serotonin 1D (5-HT1D) agonists and other agents in acute migraine. Neurol. Clin., 15.1 (1997): 61-83.

Matsumura et al., Surface activities, biodegradability and antimicrobial properties of n-alkyl glucosides, mannosides and galactosides. Journal of the America Oil Chemists Society, 67.12 (1990): 996-1001.

Mitrano et al. Factors affecting insulin adherence to type I glass bottles. Am. J. Hasp. Pharm., 39.9 (1982): 1491-5.

Moses et al., Insulin Administered Intranasally as an Insulin-Bite Salt Aerosol—Effectiveness and Reproducibility in Normal and Diabetic Subjects. Diabetes, 32 (1983): 1040-1047.

Murakami et al., Assessment of Enhancing Ability of Medium-Chain Alkyl Saccharides as New Absorption Enhancers in Rat Rectum. International Journal of Pharmaceutics, 79.1-3 (1992): 159-169.

Newman., Aerosol deposition consideration in inhalation therapy. Chest, (1985): 152S-160S.

O'Donnell et al., Therapeutic potential of a long acting somatostatin analogue in gastrointestinal diseases. Gut, 30.9 (1989): 1165-72.

Ogiso et al., Percutaneous Absorption of Elcatonin Chemical and Hypocalcemic Effect in Rat. Chemical & Pharmaceutical Bulletin, The Pharmaceutical Society of Japan, Tokyo, Japan, 39.2 (1991): 449-453.

Olesen et al., The Headaches. Lippincott Williams & Wilkins, (2005): 474.

Paulsson et al., Controlled drug release from Gels using surfactant aggregates. II Vesicles formed from mixtures of amphiphilic drugs and oppositely charged surfactants. Pharm, Res., 18.11 (2001): 1586-1592.

PCT/US2008/62961 International Preliminary Report on Patentability dated Nov. 10, 2009.

PCT/US2008/62961 International Search Report dated Jul. 25, 2008.

PCT/US2009/38696 International Preliminary Report on Patentability dated Sep. 28, 2010.

PCT/US2009/38696 International Search Report dated Sep. 28, 2009.

PCT/US2011/056735 International Search Report dated Jun. 20, 2012.

PCT/US2012/042311 International Search Report dated Aug. 31, 2012.

PCT/US2014/070944 International Search Report dated Apr. 15, 2015.

Phillips., The challenge of gene therapy and DNA delivery. J. Pharm Pharmacology, 53.9 (2001): 1169-1174.

Pillion et al., Synthetic long-chain alkyl maltosides and alkyl sucrose esters as enhancers of nasal insulin absorption. J. Pharm. Sci., 91 (2002): 1456-1462.

Pillion et al., Systemic Absorption of Insulin Delivered Topically to the Rat Eye. Investigative Ophthalmology & Visual Science, 32.12 (1991): 3021-3027.

Pirollo et al. Targeted delivery of small interfering RNA: approaching effective cancer therapies. Cancer Res., 68.5 (2008): 1247-1250.

Richards., Inactivation of resistant Pseudomonas aeruginosa by antibacterial combinations. J. Pharm. Pharmacol., 23 (1971): 136S-140S.

Salem et al., Approaches to the Pharmacological Treatment of Obesity. Expert Review of Clinical Pharmacology, 3.1 (2010): 73-88., accessed online from http://vvww.medscape.com on Feb. 5, 2010.

Salzman et al., Intranasal Aerosolized Insulin. The New England Journal of Medicine, 312.17 (1985): 1078-1084.

Sanders et al., Pharmacokinetics of ergotamine in healthy volunteers following oral and rectal dosing. Eur. J. Clin. Pharmacol., 30.3 (1986): 331-334.

Schmidt, Richard R. et al., New Methods for the Synthesis of Glycosides and Oligosaccharides: Are There Alternatives to the Koenigs-Knorr Method? Angew. Chem. Int. Ed. Engl. 25 (1986): 212-235.

Senel et al., Drug permeation enhancement via buccal route: possibilities and limitations. Journal of Controlled Release 72 (2001): 133-144.

Shim et al., Administration Route Dependent Bioavailability of Interferon-α and Effect of Bile Salts on the Nasal Absorption. Drug Development and Industrial Pharmacy, 19.10 (1993): 1183-1199.

Stevens et al., Use of Glucagon to Treat Neonatal Low-Output Congestive Heart Failure after Maternal Labetalol Therapy. The Journal of Pediatrics, 127.1 (1995): 151-153.

Swarbrick et al., Encyclopedia of Pharmaceutical Technology. Informa Health Care, 2nd edition, 1 (2002): 918.

Tillman et al., Oral Delivery of Antisense Oligonucleotide in Man. J. Pharm. Sci., 97.1 (2008): 225-236, published online Aug. 22, 2007.

Tsuchido et al., Lysis of Bacillus subtilis Cells by Glycerol and Sucrose Esters of Fatty Acids. Applied and Environmental Microbiology, 53.3 (1987): 505-508.

Turker et al., Nasal route and drug delivery systems. Pharm. World Sci., 26.3 (2004): 137-142.

Turton et al., A role for glucagon-like peptide-1 in the central regulation of feeding. Nature, 379.6560 (1996): 69-72.

U.S. Appl. No. 12/116,842 Office action dated Apr. 2, 2013.
U.S. Appl. No. 12/116,842 Office action dated Dec. 17, 2013.
U.S. Appl. No. 12/116,842 Office Action dated Jul. 8, 2015.
U.S. Appl. No. 12/116,842 Office action dated May 25, 2011.
U.S. Appl. No. 12/116,842 Office action dated Nov. 15, 2011.
U.S. Appl. No. 12/266,529 Office action dated Jul. 10, 2012.
U.S. Appl. No. 12/266,529 Office action dated Nov. 16, 2011.
U.S. Appl. No. 12/413,439 Office Action dated Jul. 14, 2016.
U.S. Appl. No. 12/413,439 Office Action dated Mar. 30, 2017.
U.S. Appl. No. 12/413,439 Office Action dated Oct. 19, 2017.
U.S. Appl. No. 12/413,439 Office Action dated Oct. 5, 2015.
U.S. Appl. No. 12/413,439 Office action dated Jun. 19, 2014.
U.S. Appl. No. 12/413,439 Office Action dated Mar. 13, 2015.
U.S. Appl. No. 12/413,439 Office action dated Mar. 18, 2011.
U.S. Appl. No. 12/413,439 Office action dated Nov. 21, 2011.
U.S. Appl. No. 13/371,274 Office Action dated Apr. 10, 2013.
U.S. Appl. No. 13/371,274 Office Action dated Sep. 26, 2012.
U.S. Appl. No. 13/495,942 Office Action dated Oct. 1, 2013.
U.S. Appl. No. 14/021,988 Office Action dated May 22, 2015.
U.S. Appl. No. 14/152,686 Office Action dated Aug. 25, 2015.
U.S. Appl. No. 14/152,686 Office Action dated Dec. 31, 2014.
U.S. Appl. No. 14/152,686 Office Action dated Jul. 5, 2016.
U.S. Appl. No. 14/527,613 Office Action dated Apr. 21, 2017.
U.S. Appl. No. 14/527,613 Office Action dated Jul. 14, 2016.
U.S. Appl. No. 14/948,081 Office Action dated Jun. 20, 2017.
U.S. Appl. No. 14/948,081 Office Action dated Feb. 15, 2018.
U.S. Appl. No. 14/948,081 Office Action dated Oct. 31, 2016.
U.S. Appl. No. 15/470,498 Office Action dated Apr. 12, 2018.

(56) References Cited

OTHER PUBLICATIONS

Van Der Lubben et al., Chitosan and its derivatives in mucosal drug and vaccine delivery. Eur. J. Pharm. Sci., 14.3 (2001): 201-207.

Vidal et al., Making sense of antisense. European Journal of Cancer, 41.18 (2005): 2812-2818.

Watanabe et al., Antibacterial Carbohydrate Monoesters Suppressing Cell Growth of Streptoccus mutans in the Presence of Sucrose. Current Microbiology, 41.3 (2000): 210-213.

Weber., Metabolism of orally administered alkyl beta-glycosides in the mouse. J. Nutr., 114 (1984): 247-254.

Webpage for Anatrace products of Affymetrix, Downloaded on Dec. 13, 2012 from http://www.affymetrix.com/estore/browse/level_three_category_and_products.jsp?category=35843&categoryIdClicked=35843&expand=true&parent=35900.

Weidinger-Hendeles et al., Oral phenylephrine: An ineffective replacement for pseudoephedrine? J. Allergy Clin. Immunol., 118.1 (2006): 279-280.

Wermeling et al., Pharmacokinetics and pharmacodynamics of a new intranasal midazolam formulation in healthy volunteers. Anesthesia & Analgesia, 103.2 (2006): 344-349.

Yamamoto et al., The Ocular Route for Systemic Insulin Delivery in the Albino Rabbit. The Journal of Pharmacology and Experimental Therapeutics, 249.1 (1989): 249-255.

Yu Xinrui et al., Triptan Medicament and Migraine. World Pharmacy (Synthetic Drug and Biochemical Drug Formulation Fascicule), 22.2 (2001): 91-92.

U.S. Appl. No. 15/470,498 Final Office Action dated Nov. 2, 2018.

EP18171484.1 Extended European Search Report dated Oct. 30, 2018.

U.S. Pat. No. 9,763,876 Petition for Inter Partes Review (IPR2019-00449) dated Jan. 28, 2019.

U.S. Pat. No. 9,763,876 Petition for Inter Partes Review (IPR2019-00450) dated Jan. 29, 2019.

U.S. Pat. No. 9,763,876 Petition for Inter Partes Review (IPR2019-00451) dated Jan. 29, 2019.

U.S. Appl. No. 17/228,514, filed Apr. 12, 2021, first named inventor Steve Cartt.

ADMINISTRATION OF BENZODIAZEPINE COMPOSITIONS

This application is a continuation of U.S. patent application Ser. No. 17/228,514, filed Apr. 12, 2021, which is a continuation of U.S. patent application Ser. No. 15/955,397, filed Apr. 17, 2018, which is a continuation of U.S. patent application Ser. No. 12/413,439, filed Mar. 27, 2009, now Abandoned, which claims priority under 35 U.S.C. § 119(e) from U.S. Provisional Application No. 61/040,558, which was filed on Mar. 28, 2008, all of which are incorporated herein by reference in their entireties.

FIELD OF THE INVENTION

This application relates to the nasal administration of benzodiazepine drugs and combinations thereof.

BACKGROUND OF THE INVENTION

By way of non-limiting example, the benzodiazepine family consists of drugs such as diazepam, lorazepam, and medazepam. The drugs in this family have been observed as possessing sedative, tranquilizing and muscle relaxing properties. They are frequently classified as an anxiolytic and skeletal muscle relaxants. They are thought to be useful in preventing, treating, or ameliorating the symptoms of anxiety, insomnia, agitation, seizures (such as those caused by epilepsy), muscle spasms and rigidity (which can be caused by tetanus), the symptoms of drug withdrawal associated with the continuous abuse of central nervous system depressants, and exposure to nerve agents.

Benzodiazepines are thought to act by binding to the GABAA receptor of a neuron, possibly causing the receptor to change shape and making it more accessible to gamma-aminobutyric acid (GABA).

GABA is an inhibitory neurotransmitter that, when bound to the GABAA receptor, facilitates Cl$^-$ ions flooding into the neuron to which the receptor is bound. The increase in ions hyperpolarizes the membrane of the neuron. This completely or substantially reduces the ability of the neuron to carry an action potential. Targeting this receptor is particularly useful in treating many disorders, such as tetanus and epilepsy, which may result from too many action potentials proceeding through the nervous system.

Current formulations of benzodiazepine drugs can be administered orally, rectally, or parenterally. The ability to utilize these and other types of formulations has been significantly limited due, in many cases, to solubility challenges.

The oral route of administration may be considered suboptimal due to several disadvantages. For example, the amount of time required for an orally administered benzodiazepine drug to reach therapeutically relevant concentrations in blood plasma may be rather long, such as an hour or more. Moreover, as benzodiazepine drugs pass through the liver a significant amount may be metabolized. Thus, it may require large doses to achieve therapeutic plasma levels. Furthermore, due to the nature of seizures and muscle spasms, it can be extremely difficult for either a patient or a care-giver to administer the benzodiazepine drug orally.

Intravenous administration perhaps provides a faster route of administration. However intravenous administration is generally limited to trained health care professionals in tightly controlled clinical settings. Additionally, sterility must be maintained. Furthermore, administering any drug intravenously can be painful and is likely impractical for patients suffering from a phobia of needles.

Suppository compositions of benzodiazepine drugs can have a rapid onset of action. However, the inconvenience of suppositories is an obvious impediment to their being administered by anyone outside a very small group of the patient's intimate acquaintances and the patient's professional medical caretakers.

SUMMARY OF THE INVENTION

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w), preferably about 10% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w), preferably about 10% to about 70% (w/w). In some embodiments, the benzodiazepine drug is dissolved in a carrier system. In some embodiments, at least part of the benzodiazepine drug is in a form comprising benzodiazepine microparticles, nanoparticles or combinations thereof. In some embodiments, the composition is substantially free of benzodiazepine microparticles, nanoparticles or combinations thereof.

In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, medazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm. In some embodiments, the benzodiazepine drug is substantially free of benzodiazepine microparticles, nanoparticles or combinations thereof.

In some embodiments, the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, one or more alcohols are selected from the group consisting of: ethanol, propyl alcohol, butyl alcohol, pentanol, benzyl alcohol, any isomers thereof, or any combinations thereof. In some embodiments, the one or more glycols are selected from the group consisting of: ethylene glycol, propylene glycol, butylene glycol, pentylene glycol, any isomers thereof, and any combinations thereof. In some preferred embodiments, the glycols exclude glycol polymers. In some preferred embodiments, the glycols exclude glycol polymers having an average molecular weight of greater than 200. In some embodiments, the glycols exclude polyethylene glycol having an average molecular weight of greater than about 200.

In some embodiments, the benzodiazepine drug is present in the carrier system in a concentration from about 1 mg/mL to about 600 mg/mL. In some embodiments, the benzodiazepine drug is present in a carrier system in a concentration from about 10 mg/mL to about 250 mg/mL. In some embodiments, the benzodiazepine is present in a carrier system in a concentration from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w).

In some embodiments, the carrier system comprises one or more alcohols or glycols, or any combinations thereof, in an amount from about 10% to about 70% (w/w). In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, the composition comprises one or more additional excipients, such as one or more parabens, one or more povidones, and/or one or more alkyl glycosides.

The invention also discloses a method of treating a patient with a disorder that may be treatable with a benzodiazepine drug. In some embodiments, the patient is a human. In some embodiments, the method comprises: administering to one or more nasal mucosal membranes of a patient a pharmaceutical composition for nasal administration comprising a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70%, preferably about 10% to about 70% (w/w). In some embodiments, the benzodiazepine is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70%, preferably about 10% to about 70% (w/w). In some embodiments, the benzodiazepine drug is dissolved in a carrier system. In some embodiments, the benzodiazepine drug includes benzodiazepine microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, medazepam, lorazepam, prazepam, quazepam, triazolam, temazepam, loprazolam, or any pharmaceutically-acceptable salts thereof, and any combinations thereof. In some embodiments, the benzodiazepine drug is diazepam, or a pharmaceutically-acceptable salt thereof. In some embodiments, the benzodiazepine drug is fully dissolved in a single phase comprising one or more one or more natural or synthetic tocopherols or tocotrienols and one or more alcohols or glycols. In some embodiments, the benzodiazepine drug comprises benzodiazepine microparticles, nanoparticles, or combinations thereof. In some such embodiments, the composition further comprises water. In some embodiments, the benzodiazepine nanoparticles have an effective average particle size of less than about 5000 nm. In some embodiments, the composition is substantially free of benzodiazepine microparticles, nanoparticles or combinations thereof.

In some embodiments, the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof.

In some embodiments, the one or more alcohols are selected from the group consisting of: ethanol, propyl alcohol, butyl alcohol, pentanol, benzyl alcohol, any isomers thereof, and any combinations thereof. In some embodiments, the one or more glycols are selected from the group consisting of: ethylene glycol, propylene glycol, butylene glycol, pentylene glycol, any isomers thereof, and any combinations thereof. In some embodiments, the alcohol or glycol is free of water (dehydrated, USP). In some embodiments, the alcohol is ethanol (dehydrated, USP).

In some embodiments, the benzodiazepine drug is present in the carrier system in a concentration from about 1 mg/mL to about 600 mg/mL. In some embodiments, the benzodiazepine drug is present in the carrier system in a concentration of from about 10 mg/mL to about 250 mg/mL. In some embodiments, the benzodiazepine drug is present in the carrier system in a concentration of from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w).

In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount from about 30% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, the composition is in a pharmaceutically-acceptable spray formulation, and further comprising administering the composition to one or more nasal mucosal membranes of the patient. In some embodiments, the therapeutically effective amount is from about 1 mg to about 20 mg of the benzodiazepine. In some embodiments, the pharmaceutical composition is in a pharmaceutically-acceptable spray formulation having volume from about 10 µL, to 200 µL.

In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

In some embodiments, the administration of the composition begins at any time before or after onset of symptoms of a disorder which may be treatable with the composition.

Additional embodiments, uses, and advantages of the invention will become apparent to the person skilled in the art upon consideration of the disclosure set forth herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Provided herein are pharmaceutical compositions of one or more benzodiazepine drugs and methods of using such pharmaceutical compositions. Such pharmaceutical compositions are administered nasally.

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 10% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 10% to about 70% (w/w). In some embodiments, the benzodiazepine drug is dissolved in a carrier system. In some embodiments, at least part of the benzodiazepine drug is in a form of microparticles, nanoparticles, or combinations thereof. In some embodiments, the composition is substantially free of benzodiazepine microparticles, nanoparticles or combinations thereof.

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w). In some embodiments, the benzodiazepine drug is dissolved in a carrier system. In some embodiments, at least part of the benzodiazepine drug is in a form of microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, medazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm. In some embodiments, the composition is substantially free of benzodiazepine microparticles, nanoparticles or combinations thereof.

In some embodiments, the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. In some embodiments, the carrier system includes one or more synthetic tocopherols having a polymer glycol covalently bonded or linked to a tocopherol core, such as Vitamin E TPGS, which is described in U.S. Pat. No. 6,193,985, which is incorporated herein by reference in its entirety. In particular, it has been found that in some particulate suspensions of benzodiazepines, wherein the benzodiazepine is not dissolved in a tocopherol phase, Vitamin E TPGS can be a desirable excipient for stabilizing the particulate (microparticle, nanoparticle or combination) suspension. In some embodiments, on the other hand, the carrier system specifically excludes synthetic tocopherols having a polymer glycol covalently bonded or linked to a tocopherol core, such as Vitamin E TPGS, which is described in U.S. Pat. No. 6,193,985, which is incorporated herein by reference in its entirety.

In some embodiments, one or more alcohols are selected from the group consisting of: ethanol, propyl alcohol, butyl alcohol, pentanol, benzyl alcohol, any isomers thereof, or any combinations thereof. In some embodiments, the alcohol is ethanol (dehydrated, USP). In some embodiments, the one or more glycols are selected from the group consisting of: ethylene glycol, propylene glycol, butylene glycol, pentylene glycol, any isomers thereof, and any combinations thereof. In some embodiments, the glycol is propylene glycol USP. In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, the benzodiazepine drug is present in the carrier system in a concentration from about 1 mg/mL to about 600 mg/mL. In some embodiments, the benzodiazepine drug is present in a carrier system in a concentration from about 10 mg/mL to about 250 mg/mL. In some embodiments, the benzodiazepine is present in a carrier system in a concentration from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w). In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, the carrier system comprises one or more alcohols or glycols, or any combinations thereof, in an amount from about 10% to about 55%, about 10% to about 40%, about 10% to about 35%, about 12% to about 55%, about 12% to about 40%, about 12% to about 35%, about 15% to about 55%, about 15% to about 40%, about 15% to about 35%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5% or about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w). In some embodiments, the alcohol is ethanol or contains ethanol. In some preferred embodiments, the glycols exclude glycol polymers. In some preferred embodiments, the glycols exclude glycol polymers having an average molecular weight of greater than 200. In some embodiments, the glycols exclude polyethylene glycol having an average molecular weight of greater than 200.

In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, the compositions comprise at least one alkyl glycoside. In some embodiments, the at least one alkyl glycoside is one described in U.S. Pat. No. 5,661,130, which is incorporated by reference herein.

In some embodiments, the composition comprises a benzodiazepine drug that is fully dissolved in a solvent comprising a natural or synthetic tocopherol or tocotrienol, and an alcohol or glycol. In some embodiments, the composition comprises a benzodiazepine drug that is fully dissolved in a solvent comprising a natural or synthetic tocopherol or tocotrienol and an alcohol or glycol, wherein the solution is at least substantially free of water. (In some embodiments, "substantially free of water" indicates that the solution contains less than about 1%, less than about 0.5%, less than about 0.25% or less than about 0.1% water.) In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides. In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides wherein the solution is at least substantially free of water. (In some embodiments, "substantially free of water" indicates that the solution contains less than about 1%, less than about 0.5%, less than about 0.25% or less than about 0.1% water.) In some embodiments, the composition consists of a benzodiazepine dissolved in a solvent consisting of one or more natural or synthetic tocopherols or tocotrienols, one or more alcohols or glycols, and optionally one or more alkyl glycosides. In some embodiments, the composition consists of a benzodiazepine dissolved in a solvent consisting of one or more natural or synthetic tocopherols or tocotrienols, one or more alcohols or glycols, and optionally one or more alkyl glycosides, wherein the solution is at least substantially free of water. (In some embodiments, "substantially free of water" indicates that the solution contains less than about 1%, less than about 0.5%, less than about 0.25% or less than about 0.1% water.)

In some embodiments, the composition comprises a benzodiazepine drug that is fully dissolved in a solvent comprising a natural or synthetic tocopherol or tocotrienol, and an alcohol or glycol. Thus, in some embodiments, the composition is substantially free of benzodiazepine microparticles, nanoparticles or combinations thereof. In some embodiments, the composition comprises a benzodiazepine drug that is fully dissolved in a solvent comprising a natural or synthetic tocopherol or tocotrienol and an alcohol or glycol, wherein the solution is at least substantially free of water. (In some embodiments, "substantially free of water" indicates that the solution contains less than about 1%, less than about 0.5%, less than about 0.25% or less than about 0.1% water.) In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides. In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides wherein the solution is at least substantially free of water. (In some embodiments, "substantially free of water" indicates that the solution contains less than about 1%, less than about 0.5%, less than about 0.25% or less than about 0.1% water.) In some embodiments, the composition consists of a benzodiazepine dissolved in a solvent consisting of one or more natural or synthetic tocopherols, one or more alcohols or glycols, and optionally one or more alkyl glycosides. In some embodiments, the composition consists of a benzodiazepine dissolved in a solvent consisting of one or more natural or synthetic tocopherols, one or more alcohols or glycols, and optionally one or more alkyl glycosides, wherein the solution is at least substantially free of water. (In some embodiments, "substantially free of water" indicates that the solution contains less than about 1%, less than about 0.5%, less than about 0.25% or less than about 0.1% water.)

In some embodiments, the composition contains a benzodiazepine drug that at least partially in a particulate form suspended in a carrier system containing a natural or synthetic tocopherol or tocotrienol and one or more alcohols or glycols. In some embodiments, substantially all the benzodiazepine drug is in a particulate form. In some embodiments, at least part of the benzodiazepine drug is in a microparticulate or nanoparticulate form. The carrier system is one in which the amount of at least one benzodiazepine present in the composition exceeds its solubility in the carrier system. In some embodiments, a carrier system in such a composition includes water. In some embodiments, such a liquid carrier system contains water and one or more excipients. In some embodiments, one or more excipients are dissolved or suspended in the carrier system. In some embodiments, at least one such excipient stabilizes the suspension of benzodiazepine particulates in the carrier system. In some embodiments, the carrier system may contain varying concentrations of parabens (e.g. methylparaben, propylparaben, etc.), and/or varying amounts of one or more surfactants, such as povidone (polyvinyl pyrrolidinone). In some embodiments, benzodiazepine particulate suspensions specifically exclude one or more polymeric glycols, such as polyethylene glycol. In some embodiments, benzodiazepine particulate suspensions specifically exclude one or more polymeric glycols having a molecular weight greater than about 200 g/mol. In some embodiments, the composition comprises a benzodiazepine drug in a form including benzodiazepine microparticles and/or nanoparticles suspended in a carrier system comprising synthetic tocopherol, one or more parabens, one or more alcohols or glycols, one or more surfactants and water. In some embodiments, the composition comprises a benzodiazepine drug in a form including benzodiazepine microparticles or nanoparticles suspended in a carrier system comprising Vitamin E TPGS, one or both of methylparaben and propylparaben, at least one glycol, povidone and water. In some embodiments, the composition comprises a benzodiazepine drug in a form including benzodiazepine microparticles and/or nanoparticles suspended in a carrier system comprising Vitamin E TPGS, methylparaben, propylparaben, propylene glycol, povidone and water. In some embodiments, the composition consists essentially of a benzodiazepine drug in a form including benzodiazepine microparticles and/or nanoparticles suspended in a carrier system consisting essentially of a synthetic tocopherol, one or more parabens, one or more alcohols or glycols, one or more surfactants and water. In some embodiments, the composition consists essentially of a benzodiazepine drug in a form including benzodiazepine microparticles or nanoparticles suspended in a carrier system consisting essentially of Vitamin E TPGS, one or both of methylparaben and propylparaben, at least one glycol, povidone and water. In some embodiments, the composition consists essentially of a benzodiazepine drug in a form including benzodiazepine microparticles and/or nanoparticles suspended in a carrier system consisting essentially of Vitamin E TPGS, methylparaben, propylparaben, propylene glycol, povidone and water. In some embodiments, the composition consists of a benzodiazepine drug in a form including benzodiazepine microparticles and/or nanoparticles suspended in a carrier system consisting of a synthetic tocopherol, one or more parabens, one or more alcohols or glycols, one or more surfactants and water. In some embodiments, the composition consists of a benzodiazepine drug in a form including benzodiazepine microparticles or nanoparticles suspended in a carrier system consisting of Vitamin E TPGS, one or both of methylparaben and propylparaben, at least one glycol, povidone and water. In some embodiments, the composition consists of a benzodiazepine drug in a form including benzodiazepine microparticles and/or nanoparticles suspended in a carrier system consisting of Vitamin E TPGS, methylparaben, propylparaben, propylene glycol, povidone and water.

In some embodiments, the composition contains a benzodiazepine drug that at least partially in a particulate form suspended in a carrier system containing a natural or synthetic tocopherol or tocotrienol, one or more alcohols or glycols, and an alkyl glycoside. In some embodiments, substantially all the benzodiazepine drug is in a particulate form. In some embodiments, at least part of the benzodiazepine drug is in a microparticulate or nanoparticulate form. The carrier system is one in which the amount of at least one benzodiazepine present in the composition exceeds its solubility in the carrier system. In some embodiments, a carrier system in such a composition includes water. In some embodiments, such a liquid carrier system contains water and one or more excipients. In some embodiments, one or more excipients are dissolved or suspended in the carrier system. In some embodiments, at least one such excipient stabilizes the suspension of benzodiazepine particulates in the carrier system. In some embodiments, the carrier system may contain varying concentrations of parabens (e.g. methylparaben, propylparaben, etc.), and/or varying amounts of one or more surfactants, such as povidone (polyvinyl pyrrolidinone). In some embodiments, benzodiazepine particulate suspensions specifically exclude one or more polymeric glycols, such as polyethylene glycol. In some embodiments, benzodiazepine particulate suspensions specifically exclude one or more polymeric glycols having a molecular weight greater than about 200 g/mol. In some embodiments, the composition comprises a benzodiazepine drug in a form including benzodiazepine microparticles and/or nanoparticles suspended in a carrier system comprising a synthetic tocopherol, one or more parabens, one or more alcohols or glycols, an alkyglycoside and water. In some embodiments, the composition comprises a benzodiazepine drug in a form including benzodiazepine microparticles or nanoparticles suspended in a carrier system comprising Vitamin E TPGS, one or both of methylparaben and propylparaben, at least one glycol, an alkyl glycoside and water. In some embodiments, the composition comprises a benzodiazepine drug in a form including benzodiazepine microparticles and/or nanoparticles suspended in a carrier system comprising Vitamin E TPGS, methylparaben, propylparaben, propylene glycol, an alkyl glycoside and water. In some embodiments, the composition consists essentially of a benzodiazepine drug in a form including benzodiazepine microparticles and/or nanoparticles suspended in a carrier system consisting essentially of a synthetic tocopherol, one or more parabens, one or more alcohols or glycols, an alkyl glycoside, optionally a surfactant, and water. In some embodiments, the composition consists essentially of a benzodiazepine drug in a form including benzodiazepine microparticles or nanoparticles suspended in a carrier system consisting essentially of Vitamin E TPGS, one or both of methylparaben and propylparaben, at least one glycol, an alkyl glycoside, optionally a povidone and water. In some embodiments, the composition consists essentially of a benzodiazepine drug in a form including benzodiazepine microparticles and/or nanoparticles suspended in a carrier system consisting essentially of Vitamin E TPGS, methylparaben, propylparaben, propylene glycol, an alkyl glycoside, optionally a povidone, and water. In some embodiments, the composition consists of a benzodiazepine drug in a form including benzodiazepine microparticles and/or nanoparticles suspended in a carrier system consisting of a synthetic tocopherol, one or more parabens, one or more alcohols or glycols, an alkyl glycoside, optionally one or more surfactants, and water. In some embodiments, the composition consists of a benzodiazepine drug in a form including benzodiazepine microparticles or nanoparticles suspended in a carrier system consisting of Vitamin E TPGS, one or both of methylparaben and propylparaben, at least one glycol, an alkyl glycoside, optionally a povidone and water. In some embodiments, the composition consists of a benzodiazepine drug in a form including benzodiazepine microparticles and/or nanoparticles suspended in a carrier system consisting of Vitamin E TPGS, methylparaben, propylparaben, propylene glycol, an alkyl glycoside, optionally a povidone and water.

The invention also discloses a method of treating a patient with a disorder that may be treatable with a benzodiazepine drug. In some embodiments, the patient is a human. In some embodiments, the method comprises: administering to one or more nasal mucosal membranes of a patient a pharmaceutical composition for nasal administration comprising a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w), preferably about 10% to about 70% (w/w). In some embodiments, the benzodiazepine is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w), preferably about 10% to about 70% (w/w). In some embodiments, the benzodiazepine drug is dissolved in a carrier system. In other embodiments, at least part of the benzodiazepine drug is in a form including microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, medazepam, lorazepam, prazepam, quazepam, triazolam, temazepam, loprazolam, or any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm.

In some embodiments, the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. A synthetic tocopherol may include a tocopherol that has been modified to include a hydrophilic group, such as a polyethylene glycol group, which may be directly covalently bonded to the tocopherol or may be linked to the tocopherol through a covalent linking group, such as a diacid. An exemplary synthetic tocopherol of this type is Vitamin E Polyethylene Glycol Succinate (Vitamin E TPGS), although the person skilled in the art will be able to envision other synthetic tocopherols that have similar diacid and/or hydrophilic groups.

In some embodiments, the one or more alcohols are selected from the group consisting of: ethanol, propyl alcohol, butyl alcohol, pentanol, benzyl alcohol, any isomers thereof, and any combinations thereof. In some embodiments, the one or more glycols are selected from the group consisting of: ethylene glycol, propylene glycol, butylene glycol, pentylene glycol, any isomers thereof, and any combinations thereof. In some embodiments, one or more glycols specifically excludes polymeric glycols, such as polyethylene glycol. In some embodiments, one or more glycols specifically excludes a polymeric glycol having a molecular weight of greater than about 200 g/mol.

In some embodiments, the benzodiazepine drug is present in the carrier system in a concentration from about 1 mg/mL to about 600 mg/mL. In some embodiments, the benzodiazepine drug is present in the carrier system in a concentration of from about 10 mg/mL to about 250 mg/mL. In some embodiments, the benzodiazepine drug is present in the carrier system in a concentration of from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w). In some embodiments, especially where particulate suspensions of a benzodiazepine drug are contemplated, the compositions may include a tocopherol, especially a synthetic tocopherol having a hydrophilic group covalently linked to a tocopherol. In other embodiments, especially where a solution of benzodiazepine drug is contemplated, the tocopherol is substantially or completely free of Vitamin E TPGS.

In some embodiments, the carrier system comprises one or more alcohols or glycols, or any combinations thereof, in an amount from about 10% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount from about 30% (w/w). In some embodiments the amount of one or more alcohols or glycols in the carrier system is about 10% to about 55%, about 10% to about 40%, about 10% to about 35%, about 12% to about 55%, about 12% to about 40%, about 12% to about 35%, about 15% to about 55%, about 15% to about 40%, about 15% to about 35%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5% or about 55% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, a composition comprises at least one penetration enhancer in addition to a benzodiazepine drug, a natural or synthetic tocopherol or tocotrienol, and an alcohol or glycol. In some embodiments, the penetration enhancer is an alkyl glycoside. In some embodiments, the alkyl glycoside refers to any sugar joined to any hydrophobic alkyl, as described in U.S. Pat. No. 5,661,130, which is incorporated herein by reference in its entirety. The hydrophobic alkyl can be any suitable length, for example about 9 to about 24 carbons in length, especially about 10 to about 14 carbons in length. The hydrophobic alkyl can be branched and/or partially or wholly unsaturated. The alkyl may be joined to the saccharide core for example through a carbonyl group, whereby an ester group may be formed. A suitable alkyl glycoside will have the characteristics of being nontoxic, nonionic, and capable of increasing the absorption of a benzodiazepine drug when it is administered intranasally as described herein. Exemplary saccharides that may be covalently joined to an alkyl according to the present invention include glucose, maltose, maltotriose, maltotetrose, sucrose and trehalose. Exemplary alkyl glycosides that may be employed include octyl-, nonyl-, decyl-, undecyl-, dodecyl, tridecyl, tetradecyl, pentadecyl, octadecyl α- or β-D-maltoside, -glucoside or sucroside. In some embodiments, the preferred glycosides include maltose, sucrose or glucose linked by glycosidic linkage to an alkyl chain of 9, 10, 12, 14, 16, 18 or 20 carbon atoms. Where present, the amount of alkyl glycoside in the composition is sufficient to enhance the absorption of a benzodiazepine drug administered by the intranasal route. In some embodiments, the amount of alkyl glycoside in the composition is selected so as to enhance absorption of the benzodiazepine drug, while at the same time not significantly irritating the nasal mucosa. In some embodiments, the amount of alkyl glycoside in the composition is in a range of about 0.01% (w/v) to about 1% (w/v). In some embodiments, the amount of alkyl glycoside in the composition is in a range of about 0.05% (w/v) to about 0.5% (w/v), or about 0.125% (w/v) to about 0.5% (w/v).

In some embodiments, the composition is in a pharmaceutically-acceptable spray formulation, and further comprising administering the composition to one or more nasal mucosal membranes of the patient. In some embodiments, the therapeutically effective amount is from about 1 mg to about 20 mg of the benzodiazepine. In some embodiments, the pharmaceutical composition is in a pharmaceutically-acceptable spray formulation having volume from about 10 μL to 200 μL.

In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

In some embodiments, the administration of the composition begins at any time before or after onset of symptoms of a disorder which may be treatable with the composition.

Definitions

As used herein the phrase "therapeutically effective amount" (or more simply "effective amount") includes an amount sufficient to provide a specific therapeutic response for which the drug is administered to a patient in need of particular treatment. The skilled clinician will recognize that the therapeutically effective amount of drug will depend upon the patient, the indication and the particular drug administered.

As used herein, the modifier "about" is intended to have its regularly recognized meaning of approximately. In some embodiments, the term may be more precisely interpreted as meaning within a particular percentage of the modified value, e.g. "about" may in some embodiments mean±20%, ±10%, ±5%, ±2%, or ±1% or less.

As used herein, the phrase "analogs or derivatives" includes molecules that differ from one another molecule due to one or more atoms or functional groups having been replaced with a different atom or functional group. This may result in molecules with similar chemical formulas but different chemical and/or biological properties.

As used herein, the term, "isomer" includes molecules with identical chemical formulas, but between which the arrangement of the molecules may vary. These varying arrangements may result in molecules with identical chemical formulas but different chemical properties. By way of non-limiting example, propanol has the chemical formula $C_3H_7OH$. It may be found as propan-1-ol, wherein the —OH is found attached to an end carbon. Alternatively, it may be found as propan-2-ol, wherein the —OH is found attached to the second carbon.

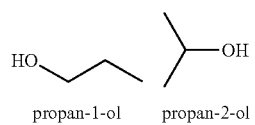

propan-1-ol    propan-2-ol

As used herein, the term "seizure" includes commonly recognized types of seizures, including absence seizures, myoclonic seizures, clonic seizures, tonic seizures, tonic-clonic seizures, and atonic seizures. Often seizures, particularly severe tonic or tonic-clonic seizures, will be presaged by one or more aura that will be familiar to the patient or those familiar with the patient. Each patient will generally experience a different type of aura, which is unique to the patient; however auras may be classified as audible, visual, olfactory or tactile sensations that usually, or at least often, precedes a patient's experiencing a seizure. (Not all patients who suffer seizures experience aura; however aura are not uncommon amongst those who suffer the worst type of seizures, especially tonic-clonic seizures.)

As used herein, the term "prevention" refers to a forestalling, including temporary forestalling, of the onset of a disorder. In the case of seizures, this can occur either with or without the benefit of a warning aura.

As used herein, the term "treatment" refers to a reduction in the intensity and/or duration of a disorder, or similar effects. The term also encompasses the side-effects of such a "treatment."

As used herein, unless otherwise qualified, "a" and "an" can mean one or more.

As used herein, the term "comprising" in all its variants, is a transitional phrase used in a claim to indicate that the invention includes or contains, but is not limited to, the specifically recited claim elements.

As used herein, the phrase "consisting essentially of" is a transitional phrase used in a claim to indicate that the a following list of ingredients, parts or process steps must be present in the claimed composition, machine or process, but that the claim is open to unlisted ingredients, parts or process steps that do not materially affect the basic and novel properties of the invention.

As used herein, the term "consisting of" is a transitional phrase used in a claim to indicate that the claimed invention includes only those elements set forth in the claim.

Benzodiazepine Drugs

In the context of the present invention, the term "benzodiazepine drug" includes any therapeutically effective benzodiazepine compound, or pharmaceutically acceptable salt, or combinations thereof. In some embodiments, benzodiazepine comprises a member of the group consisting of alprazolam, diazepam, flurazepam, lorazepam, medazepam, mexazolam, midazolam, temazepam and pharmaceutically acceptable salts and combinations thereof.

It should be recognized by those of skill in the art that additional benzodiazepine compounds that have heretofore been considered to have marginal or little therapeutic benefit, either because of low bioavailability, poor pharmacokinetic properties or poor pharmacodynamic properties, may find use through the present invention, which can provide for improved bioavailability of benzodiazepine drugs, delivery of higher concentrations of benzodiazepine drugs via the nasal route, faster attainment of therapeutic levels of benzodiazepine in the blood plasma, avoidance of the liver portal vein and concomitant avoidance of first pass effects and/or faster presentation of benzodiazepine drug to the brain.

For example, most benzodiazepines are so slightly soluble in water that a therapeutically effective amount cannot be dissolved in a volume of aqueous solvent that is amenable to application to a mucosal membrane. By use of the present carrier system, which in some embodiments, provides an improved ability to dissolve benzodiazepine drugs, the present invention allows benzodiazepine drugs to be administered to one or more mucosal membranes, including to nasal mucosal membranes. This can allow one to administer the drug without hospitalization or unnecessary discomfort. Additionally, in some embodiments of the present invention, such as nasal administration, the digestive system largely may be bypassed. This latter improvement can yield improved bioavailability, faster attainment of therapeutic levels of benzodiazepine in the blood plasma, avoidance of the liver portal vein, and/or concomitant avoidance of first pass effects.

Nasal administration of the composition can result in faster presentation of the one or more benzodiazepine drugs to the brain due to the close proximity of the membranes and the brain. A seizing patient, for example, suffers from rigid muscles and uncontrollable movement. This can make oral and/or intravenous administration difficult or inconvenient. However, the nasal passageways remain open and easily accessible, and therefore is a useful route of administration for of the present invention.

In some embodiments, the pharmaceutical composition is used to treat a patient suffering from a disorder that is amenable to treatment or prevention with an effective amount of the one or more benzodiazepine drugs. By way of non-limiting example such disorders can include: insomnia, anxiety, seizures, muscle spasms and rigidity, and the symptoms of drug withdrawal.

In some embodiments, the one or more benzodiazepine drugs, are used alone or in combination with another anticonvulsant drug to treat seizure, protect against seizure, reduce or ameliorate the intensity of seizure, reduce or ameliorate the frequency of seizure, and/or prevent occurrence or re-occurrence of seizure.

Alprazolam (8-chloro-6-phenyl-1-methyl-4H-1,2,4-triazolo[4,3-a][1,4]benzodiazepine)

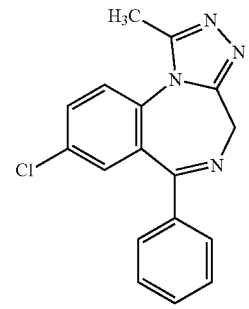 [SMILES: Cc1nnc2n1-c1ccc(Cl)cc1C(c1ccccc1)=NC2]

Alprazolam is a benzodiazepine drug having sedative, tranquilizing and muscle relaxing properties. It is classified as an anxiolytic. Alprazolam has also been shown to be useful in the treatment of panic disorder. The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

In some embodiments, alprazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, alprazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Alprazolam may be administered by the patient or other person (such as a healthcare professional) while the patient is in a non-seizing state to protect against seizure. Even where protection against seizure is not absolute, administration of alprazolam may reduce or ameliorate the intensity of seizure and/or reduce or ameliorate the frequency of seizure. In some embodiments, administration of alprazolam may prevent occurrence of seizure. In some embodiments, especially where the patient is prone to experiencing serial seizures or status epilepticus, administration of alprazolam may aid in interrupting the seizure cycle and may thus prevent the re-occurrence of seizure. In addition to the benzodiazepines (such as diazepam), other anti-convulsant drugs may be combined with alprazolam to provide an anticonvulsant or synergistic anticonvulsant effect.

Alprazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the alprazolam formulations of the invention, and in particular nasal formulations, provide fast onset of therapeutic benefit—in some instances less than about 30 minutes, less than about 15 minutes, less than about 10 minutes, and in some cases less than about 5 minutes. The alprazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Diazepam (7-chloro-1-methyl-5-phenyl-1,3-dihydro-2H-1,4-benzodiazepin-2-one)

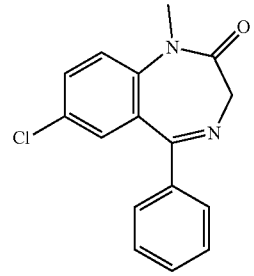 [SMILES: CN1C(=O)CN=C(c2ccccc2)c2cc(Cl)ccc21]

Diazepam is a benzodiazepine drug having sedative, tranquilizing and muscle relaxing properties. It is classified as an anxiolytic and skeletal muscle relaxant. It possesses anxiolytic, anticonvulsant, sedative, skeletal muscle relaxant and amnesic properties. The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. No. 3,371,085; 3,109,843; 3,136,815 or 3,102,116, each of which is incorporated herein by reference in its entirety.

In some embodiments, diazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, diazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Diazepam may be administered by the patient or other person (such as a healthcare professional) while the patient is in a non-seizing state to protect against seizure. Even where protection against seizure is not absolute, administration of diazepam may reduce or ameliorate the intensity of seizure and/or reduce or ameliorate the frequency of seizure. In some embodiments, administration of diazepam may prevent occurrence of seizure. In some embodiments, especially where the patient is prone to experiencing serial seizures or status epilepticus, administration of diazepam may aid in interrupting the seizure cycle and may thus prevent the re-occurrence of seizure. In addition to the benzodiazepines (such as diazepam), other anti-convulsant drugs may be combined with diazepam to provide a synergistic anticonvulsant effect.

Diazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the diazepam formulations of the invention, and in particular nasal formulations, provide fast onset of therapeutic benefit—in some instances less than about 30 minutes, less than about 15 minutes, less than about 10 minutes, and in some cases less than about 5 minutes. The diazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Flurazepam (7-chloro-5-(2-flurophenyl)-2,3-dihydro-1-(2-(diethylamino)ethyl)-1H-1,4-benzodiazepin-2-one)

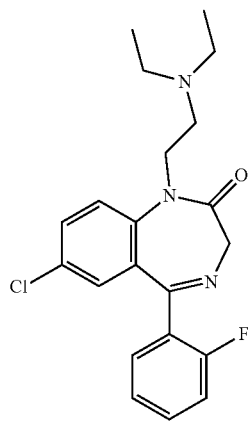 [SMILES: CCN(CC)CCN1C(=O)CN=C(c2ccccc2F)c2cc(Cl)ccc21]

Flurazepam is a benzodiazepine drug having sedative (especially soporific and hypnotic), anxiolytic, anticonvulsant and muscle relaxing properties. It is classified as an sedative, hypnotic. Flurazepam has been shown to be useful in the treatment of insomnia. The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. No. 3,567,710 or 3,299,053, each of which is incorporated herein by reference in its entirety.

In some embodiments, flurazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, flurazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Flurazepam may be administered by the patient or other person (such as a healthcare professional) while the patient is in a non-seizing state to protect against seizure. Even where protection against seizure is not absolute, administration of flurazepam may reduce or ameliorate the intensity of seizure and/or reduce or ameliorate the frequency of seizure. In some embodiments, administration of flurazepam may prevent occurrence of seizure. In some embodiments, especially where the patient is prone to experiencing serial seizures or status epilepticus, administration of flurazepam may aid in interrupting the seizure cycle and may thus prevent the re-occurrence of seizure. In addition to the benzodiazepines (such as diazepam), other anti-convulsant drugs may be combined with flurazepam to provide a synergistic anticonvulsant effect.

Flurazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the flurazepam formulations of the invention, and in particular nasal formulations, provide fast onset of therapeutic benefit—in some instances less than about 30 minutes, less than about 15 minutes, less than about 10 minutes, and in some cases less than about 5 minutes. The flurazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Lorazepam (7-chloro-5-(2-chlorophenyl)-3-hydroxy-1,3-dihydro-2H-1,4-benzodiazepin-2-one)

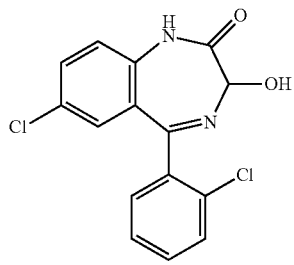 [SMILES: O=C1Nc2ccc(Cl)cc2C(c2ccccc2Cl)=NC1O]

Lorazepam is a benzodiazepine drug having sedative, tranquilizing, anticonvulsant, amnesic and muscle relaxing properties. It is classified as an anxiolytic. Lorazepam has also been shown to be useful in the treatment of nausea. The dosage of lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

In some embodiments, lorazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, lorazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Lorazepam may be administered by the patient or other person (such as a healthcare professional) while the patient is in a non-seizing state to protect against seizure. Even where protection against seizure is not absolute, administration of lorazepam may reduce or ameliorate the intensity of seizure and/or reduce or ameliorate the frequency of seizure. In some embodiments, administration of lorazepam may prevent occurrence of seizure. In some embodiments, especially where the patient is prone to experiencing serial seizures or status epilepticus, administration of lorazepam may aid in interrupting the seizure cycle and may thus prevent the re-occurrence of seizure. In addition to the benzodiazepines (such as diazepam), other anti-convulsant drugs may be combined with lorazepam to provide a synergistic anticonvulsant effect.

Lorazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the lorazepam formulations of the invention, and in particular nasal formulations, provide fast onset of therapeutic benefit—in some instances less than about 30 minutes, less than about 15 minutes, less than about 10 minutes, and in some cases less than about 5 minutes. The lorazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Medazepam ((7-chloro-1-methyl-5-phenyl-2,3-dihydro-1H-1,4-benzodiazepine)

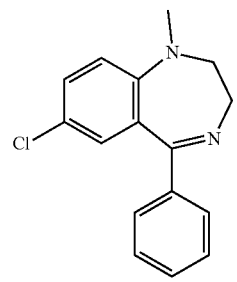 [SMILES: CN1CCN=C(c2ccccc2)c2cc(Cl)ccc21]

Medazepam is a benzodiazepine drug having sedative, tranquilizing, anticonvulsant, amnesic and muscle relaxing properties. It is classified as an anxiolytic. Medazepam has also been shown to be useful in the treatment of nausea. The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

In some embodiments, medazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, medazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Medazepam may be administered by the patient or other person (such as a healthcare professional) while the patient is in a non-seizing state to protect against seizure. Even where protection against seizure is not absolute, administration of medazepam may reduce or ameliorate the intensity of seizure and/or reduce or ameliorate the frequency of seizure. In some embodiments, administration of medazepam may prevent occurrence of seizure. In some embodiments, especially where the patient is prone to experiencing serial seizures or status epilepticus, administration of medazepam may aid in interrupting the seizure cycle and may thus prevent the re-occurrence of seizure. In addition to the benzodiazepines (such as diazepam), other anti-convulsant drugs may be combined with medazepam to provide a synergistic anticonvulsant effect.

Medazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the medazepam formulations of the invention, and in particular nasal formulations, provide fast onset of therapeutic benefit—in some instances less than about 30 minutes, less than about 15 minutes, less than about 10 minutes, and in some cases less than about 5 minutes. The medazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Mexazolam (10-Chloro-11b-(2-chlorophenyl)-1,3,7,11b-tetrahydro-3-methyloxazolo[3,2-d][1,4]benzodiazepin-6(5H)-one)

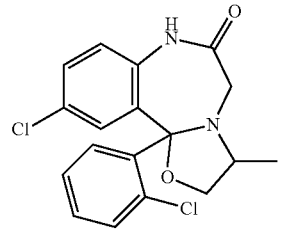 [SMILES: CC1COC2(c3ccccc3Cl)c3cc(Cl)ccc3NC(=O)CN12]

Mexazolam is a benzodiazepine drug having sedative, tranquilizing, anticonvulsant, amnesic and muscle relaxing properties. It is classified as an anxiolytic. Mexazolam has also been shown to be useful in the treatment of nausea. The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

In some embodiments, mexazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, mexazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Mexazolam may be administered by the patient or other person (such as a healthcare professional) while the patient is in a non-seizing state to protect against seizure. Even where protection against seizure is not absolute, administration of mexazolam may reduce or ameliorate the intensity of seizure and/or reduce or ameliorate the frequency of seizure. In some embodiments, administration of mexazolam may prevent occurrence of seizure. In some embodiments, especially where the patient is prone to experiencing serial seizures or status epilepticus, administration of mexazolam may aid in interrupting the seizure cycle and may thus prevent the re-occurrence of seizure. In addition to the benzodiazepines (such as diazepam), other anti-convulsant drugs may be combined with mexazolam to provide a synergistic anticonvulsant effect.

Mexazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the mexazolam formulations of the invention, and in particular nasal formulations, provide fast onset of therapeutic benefit—in some instances less than about 30 minutes, less than about 15 minutes, less than about 10 minutes, and in some cases less than about 5 minutes. The mexazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Midazolam (8-chloro-6-(2-fluorophenyl)-1-methyl-4H-imidazo(1,5-a)benzodiazepine)

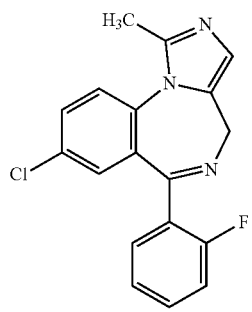 [SMILES: Cc1ncc2n1-c1ccc(Cl)cc1C(c1ccccc1F)=NC2]

Midazolam is a tricyclic benzodiazepine having anxiolytic, amnesic, hypnotic, anticonvulsant, skeletal muscle relaxant and sedative properties. Midazolam is considered soluble in water at a pH lower than about 4, but is relatively insoluble in most aqueous solutions at neutral pH (e.g. about 6 to 8). Thus it is desirable in some embodiments for aqueous nasal preparations of midazolam to have a pH above about 5.5, preferably above about 6.0, or above about 6.5. In some preferred embodiments, the pH is between about 6 and 9, between about 6 and 8. It is considered that preparations of midazolam are particularly suitable for nasal administration as the lipid-soluble (at approximately neutral pH) midazolam is rapidly absorbed across nasal mucosa, leading to efficient uptake of midazolam. It is further considered that midazolam may be formulated in a non-aqueous delivery vehicle, such as is known in the aerosol administration art, such as hydrofluorocarbon propellants, hydrocarbon propellants, etc.

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. No. 4,280,957 or 5,831,089, each of which is incorporated herein by reference in its entirety.

In some embodiments, midazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, midazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Midazolam may be administered by the patient or other person (such as a healthcare professional) while the patient is in a non-seizing state to protect against seizure. Even where protection against seizure is not absolute, administration of midazolam may reduce or ameliorate the intensity of seizure and/or reduce or ameliorate the frequency of seizure. In some embodiments, administration of midazolam may prevent occurrence of seizure. In some embodiments, especially where the patient is prone to experiencing serial seizures or status epilepticus, administration of midazolam may aid in interrupting the seizure cycle and may thus prevent the re-occurrence of seizure. In addition to the benzodiazepines (such as diazepam), other anti-convulsant drugs may be combined with midazolam to provide a synergistic anticonvulsant effect.

Midazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the midazolam formulations of the invention, and in particular nasal formulations, provide fast onset of therapeutic benefit—in some instances less than about 30 minutes, less than about 15 minutes, less than about 10 minutes, and in some cases less than about 5 minutes. The midazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Temazepam (7-chloro-1-methyl-5-phenyl-3-hydroxy-1,3-dihydro-2H-1,4-benzodiazepin-2-one)

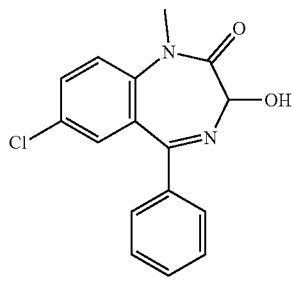 [SMILES: CN1C(=O)C(O)N=C(c2ccccc2)c2cc(Cl)ccc21]

Temazepam is a benzodiazepine drug having sedative, tranquilizing, anticonvulsant, amnesic and muscle relaxing properties. It is classified as an anxiolytic. Temazepam has also been shown to be useful in the treatment of nausea. The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. No. 3,340,253 or 3,374,225, each of which is incorporated herein by reference in its entirety.

In some embodiments, temazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, temazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Temazepam may be administered by the patient or other person (such as a healthcare professional) while the patient is in a non-seizing state to protect against seizure. Even where protection against seizure is not absolute, administration of temazepam may reduce or ameliorate the intensity of seizure and/or reduce or ameliorate the frequency of seizure. In some embodiments, administration of temazepam may prevent occurrence of seizure. In some embodiments, especially where the patient is prone to experiencing serial seizures or status epilepticus, administration of temazepam may aid in interrupting the seizure cycle and may thus prevent the re-occurrence of seizure. In addition to the benzodiazepines (such as diazepam), other anti-convulsant drugs may be combined with temazepam to provide a synergistic anticonvulsant effect.

Temazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the temazepam formulations of the invention, and in particular nasal formulations, provide fast onset of therapeutic benefit—in some instances less than about 30 minutes, less than about 15 minutes, less than about 10 minutes, and in some cases less than about 5 minutes. The temazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Pharmaceutically Acceptable Salts

Benzodiazepines have the generally basic structure of formula I:

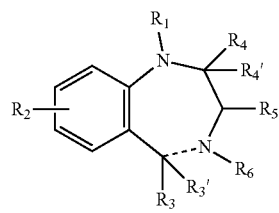

Formula I wherein $R_1$-$R_5$ are substituents. In particular embodiments, $R_1$ is an optionally substituted alkyl or forms a ring with $R_4$, $R_2$ is a halogen (e.g. Cl, Br), $R_3$ is optionally substituted aryl (e.g. 2-Chloro or 2-Fluorophenyl), $R_5$ is H or OH, $R_4$ and $R_4'$ together form a carbonyl (C=O) with the carbon to which they are attached or $R_4$ and $R_1$ form an optionally substituted heterocyclic ring with the diazepam ring atoms to which they are respectively attached; $R_3'$ and $R_6$ together form a double bond or may be combined to form an optionally substituted heterocyclic ring along with the diazepam ring atoms to which they are respectively attached. Such basic compounds may form acid addition salts with pharmaceutically acceptable acids, such as pharmaceutically acceptable mineral acids and pharmaceutically acceptable organic acids.

Pharmaceutically acceptable mineral acids include HCl, $H_2SO_4$, $H_2SO_3$, $H_3PO_4$, $H_3PO_3$, and others that will be recognized by those of skill in the art. Pharmaceutically acceptable organic acids include acetic acid, benzoic acid, tartaric acid, citric acid, oxalic acid, maleic acid, malonic acid, etc. Thus, in some embodiments, the pharmaceutically acceptable acid may be selected from the group consisting of: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acidascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acidfumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, benzenesulfonic acid (besylic acid), naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) and undecylenic acid. Other pharmaceutically acceptable acids may be pharmaceutically acceptable acidic (anionic) polymers or pharmaceutically acceptable amphoteric polymers. One skilled in the art will recognize that other basic active pharmaceutical ingredients may be combined with the foregoing acids to produce acid addition salts. Likewise the person skilled in the art will recognize that in some embodiments it may be advantageous that some or all of the added acid be an active pharmaceutical ingredient in its own right.

In some embodiments, the invention provides nasal compositions comprising one or more acidic pharmaceutically active ingredients. It is considered well within the ordinary skill in the art to determine which of the compounds set for the above are acidic. Such compounds may be prepared as base addition salts, e.g. by the addition of one or more mineral bases (e.g. NaOH, KOH, $NaHCO_3$, $Na_2CO_3$, $NH_3$) or organic bases. It is considered within the skill in the art to choose a pharmaceutically acceptable base.

Known benzodiazepine compounds have anxiolytic, anti-convulsant, sedative and/or skeletal muscle relaxant effect. The term "anticonvulsant" includes treatment of seizures, protection against seizure, reduction or amelioration of the intensity of seizure, reduction or amelioration of the frequency of seizure, and/or prevention of the occurrence or re-occurrence of seizure. In this regard, treatment of seizure includes cessation of an ongoing seizure, reduction in the severity of an ongoing seizure, reduction in the duration of an ongoing seizure. Protection against seizure includes forestalling an oncoming seizure.

Carrier System

Vitamin E is a class of fat soluble methylated phenols. There are at least eight naturally-occurring compounds that comprise this class: α-tocopherol, β-tocopherol, γ-tocopherol, δ-tocopherol, α-tocotrienol, β-tocotrienol, γ-tocotrienol, and δ-tocotrienol, all of which may be used in the compositions and methods of the present invention. There are multiple isomers of each of these compounds, all of which may be used in the compositions and methods of the present invention. There are also multiple esters of each of these compounds, including tocophersolan, all of which may be used in the compositions and methods of the present invention. As used herein, Vitamin E refers to any of the natural or synthetic tocopherols, tocotrienols, any isomers thereof, any esters thereof, any analogs or derivatives thereof, or any combinations thereof.

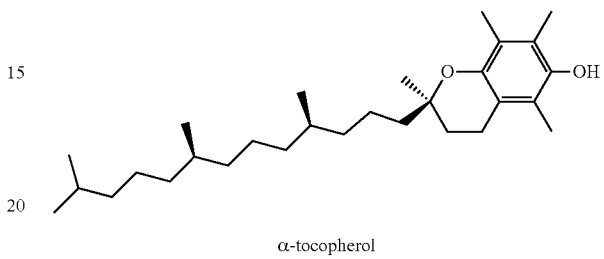

α-tocopherol

The compounds that comprise Vitamin E are antioxidants. There is also evidence that they can prevent, delay the onset of, or ameliorate the symptoms of heart disease, cancer, cataracts, macular degeneration, glaucoma, Alzheimer's, and Parkinson's disease.

The inventors have found that Vitamin E can provide an effective carrier for benzodiazepine drugs. In some embodiments, benzodiazepines are soluble, or partially soluble, in Vitamin E. In some embodiments, Vitamin E may be present as microparticles, nanoparticles, or any combination thereof. Furthermore, use of Vitamin E can have the added benefit of either avoiding irritation of sensitive mucosal membranes and/or soothing irritated mucosal membranes.

Vitamin E is generally classified as hydrophobic, and when used as a carrier may be limited to formulations as an emulsion. However, emulsions can have several drawbacks. For instance, they may be difficult to create and can be highly unstable. Additionally, they can leave an oily film on the surface of the skin. Thus, to avoid the drawbacks of emulsions, some embodiments of the present invention comprise solutions of one or more benzodiazepine drugs in Vitamin E and one or more lower alkyl alcohols or one or more lower alkyl glycols, or any combinations thereof.

Lower alkyl alcohols are those with six or fewer carbon atoms. Thus, any of ethanol, propyl alcohol, butyl alcohol, pentanol, benzyl alcohol, any isomers thereof, or any combinations thereof can be used.

Lower alkyl glycols are those with six or fewer carbon atoms. Thus, any of ethylene glycol, propylene glycol, butylene glycol, pentylene glycol, any isomers thereof, or any combinations thereof can be used.

Additional Excipients

In some embodiments, a composition comprises at least one penetration enhancer in addition to a benzodiazepine drug, a natural or synthetic tocopherol or tocotrienol, and an alcohol or glycol. In some embodiments, the penetration enhancer is at least one alkyl glycoside. In some embodiments, the alkyl glycoside refers to any sugar joined to any hydrophobic alkyl, as described in U.S. Pat. No. 5,661,130, which is incorporated herein by reference in its entirety. The hydrophobic alkyl can be any suitable length, for example about 9 to about 24 carbons in length, especially about 10 to about 14 carbons in length. The hydrophobic alkyl can be branched and/or partially or wholly unsaturated. The alkyl may be joined to the saccharide core for example through a carbonyl group, whereby an ester group may be formed. A suitable alkyl glycoside will have the characteristics of being nontoxic, nonionic, and capable of increasing the absorption of a benzodiazepine drug when it is administered intranasally as described herein. Exemplary saccharides that may be covalently joined to an alkyl according to the present invention include glucose, maltose, maltotriose, maltotetrose, sucrose and trehalose. Exemplary alkyl glycosides that may be employed include octyl-, nonyl-, decyl-, undecyl-, dodecyl, tridecyl, tetradecyl, pentadecyl, octadecyl α- or β-D-maltoside, -glucoside or sucroside. In some embodiments, the preferred glycosides include maltose, sucrose or glucose linked by glycosidic linkage to an alkyl chain of 9, 10, 12, 14, 16, 18 or 20 carbon atoms. Specific excipients that may be employed in a nasal composition according to the invention include alkylsaccharide is dodecyl maltoside, tetradecyl maltoside, sucrose dodecanoate, sucrose monostearate, sucrose distearate, and/or combinations of two or more thereof. Alkyl glycosides that are particularly considered useful in embodiments of the invention include those marketed under the name Intravail® by Aegis Therapeutics, LLC, San Diego, Calif. Other alkyl glycosides may be selected from those having a hydrophile-lipophile balance (HLB) number of from about 10-20, especially about 11-15. The HLB number may be determined as set forth in the publication US2009/0047347, published on 19 Feb. 2009, the entirety of which, and especially paragraphs [0075]-[0079], is incorporated herein by reference. Where present, the amount of alkyl glycoside in the composition is sufficient to enhance the absorption of a benzodiazepine drug administered by the intranasal route. In some embodiments, the amount of alkyl glycoside in the composition is selected so as to enhance absorption of the benzodiazepine drug, while at the same time not significantly irritating the nasal mucosa. In some embodiments, the amount of alkyl glycoside in the composition is in a range of about 0.01% (w/v) to about 1% (w/v). In some embodiments, the amount of alkyl glycoside in the composition is in a range of about 0.05% (w/v) to about 0.5% (w/v), or about 0.125% (w/v) to about 0.5% (w/v).

The term "penetration enhancer", means any material which acts to increase absorption across the mucosa and/or increases bioavailability. In some embodiments, such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect.

In some embodiments, preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. palmitoyl-dl-carnitine-chloride) is an alternative. In some embodiments, a suitable concentration is from 0.02 to 20% w/v.

In some embodiments, enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316-321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% w/v.

Thus, in some embodiments, the invention provides a pharmaceutical composition for nasal administration comprising: a benzodiazepine drug, one or more natural or synthetic tocopherols or tocotrienols, or any combinations thereof, in an amount from about 30% to about 95% (w/w); one or more alkyl glycosides; and one or more alcohols or glycols, or any combinations thereof, in an amount from about 10% to about 70% (w/w), in a pharmaceutically-acceptable formulation for administration to one or more nasal mucosal membranes of a patient. In some embodiments, the alkyl glycoside is an Intravail® brand alkyl glycoside. In some embodiments, the alkyl glycoside is dodecyl maltoside, tetradecyl maltoside, sucrose dodecanoate, sucrose monostearate, sucrose distearate, and/or a combination of two or more thereof. In some embodiments, the alkyl glycoside is dodecyl maltoside. In some embodiments, the alkyl glycoside is tetradecyl maltoside. In some embodiments, the alkyl glycoside is sucrose dodecanoate. In some embodiments, the alkyl glycoside is sucrose monostearate. In some embodiments, the alkyl glycoside is sucrose distearate. In some embodiments, the alkyl glycoside is a combination of two or more of dodecyl maltoside, tetradecyl maltoside, sucrose dodecanoate, sucrose monostearate, or sucrose distearate.

Thus, in some embodiments, the invention provides a pharmaceutical composition for nasal administration comprising: a benzodiazepine drug, which benzodiazepine drug comprises microparticles, nanoparticles or both, one or more natural or synthetic tocopherols or tocotrienols, or any combinations thereof, in an amount from about 30% to about 95% (w/w); one or more alkyl glycosides; and one or more alcohols or glycols, or any combinations thereof, in an amount from about 10% to about 70% (w/w), in a pharmaceutically-acceptable formulation for administration to one or more nasal mucosal membranes of a patient. In some embodiments, the alkyl glycoside is an Intravail® brand alkyl glycoside. In some embodiments, the alkyl glycoside is dodecyl maltoside, tetradecyl maltoside, sucrose dodecanoate, sucrose monostearate, sucrose distearate, and/or a combination of two or more thereof. In some embodiments, the alkyl glycoside is dodecyl maltoside. In some embodiments, the alkyl glycoside is tetradecyl maltoside. In some embodiments, the alkyl glycoside is sucrose dodecanoate. In some embodiments, the alkyl glycoside is sucrose monostearate. In some embodiments, the alkyl glycoside is sucrose distearate. In some embodiments, the alkyl glycoside is a combination of two or more of dodecyl maltoside, tetradecyl maltoside, sucrose dodecanoate, sucrose monostearate, or sucrose distearate.

Mucosal Membrane Preparations

Mucosal membrane preparations are generally administered in metered sprays having volumes of less than 250 μL, preferably less than 150 μL, and ideally from 25 to 100 μL. Although not prohibited in this invention, administration of volumes larger than about 300 μL per dose usually exceeds the absorption capacity of the membranes. This results in a large portion of the pharmaceutically-active ingredient being lost.

The dosage volume of preparations, in particular nasal preparations, preferably ranges from 25 to 100 μL. Volumes in excess of the aforementioned ranges may bypass the sinuses and flow down the back of the throat where the excess is swallowed.

Alprazolam

The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

As a nasal formulation, alprazolam may be administered in 25 to 250 μL metered sprays. In some preferred embodiments, alprazolam is administered in 50 to 150 μL, especially about 100 μL, metered sprays Diazepam The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085, 3,109,843, 3,136,815 or 3,102,116, each of which is incorporated herein by reference in its entirety.

As a nasal formulation, diazepam may be administered in 25 to 250 μL metered sprays. In some preferred embodiments, diazepam is administered in 50 to 150 μL, especially about 100 μL, metered sprays.

Flurazepam

The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. No. 3,567,710 or 3,299,053, each of which is incorporated herein by reference in its entirety.

As a nasal formulation, flurazepam may be administered in 25 to 250 μL metered sprays. In some preferred embodiments, flurazepam is administered in 50 to 150 μL, especially about 100 μL, metered sprays.

Lorazepam

The dosage of Lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

As a nasal formulation, lorazepam may be administered in 25 to 250 μL metered sprays. In some preferred embodiments, lorazepam is administered in 50 to 150 μL, especially about 100 μL, metered sprays.

Medazepam

The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

As a nasal formulation, medazepam may be administered in 25 to 250 μL metered sprays. In some preferred embodiments, medazepam is administered in 50 to 150 μL, especially about 100 μL, metered sprays.

Mexazolam

The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

As a nasal formulation, mexazolam may be administered in 25 to 250 μL metered sprays. In some preferred embodiments, mexazolam is administered in 50 to 150 μL, especially about 100 μL, metered sprays.

Midazolam

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. No. 4,280,957 or 5,831,089, each of which is incorporated herein by reference in its entirety.

As a nasal formulation, midazolam may be administered in 25 to 250 μL metered sprays. In some preferred embodiments, midazolam is administered in 50 to 150 μL, especially about 100 μL, metered sprays.

Temazepam

The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. No. 3,340,253 or 3,374,225, each of which is incorporated herein by reference in its entirety.

As a nasal formulation, temazepam may be administered in 25 to 250 μL metered sprays. In some preferred embodiments, temazepam is administered in 50 to 150 μL, especially about 100 μL, metered sprays.

Formulation

Some embodiments comprise administering to one or more mucosal membranes of a patient a therapeutically effective amount of one or more benzodiazepine drugs, or pharmaceutically-acceptable salts thereof. Some embodiments of the composition disclose a composition comprising one or more benzodiazepine drugs or pharmaceutically-acceptable salts thereof in a concentration up to about 600 mg/mL. Other compositions disclose a composition comprising one or more benzodiazepine drugs or pharmaceutically-acceptable salts thereof in a concentration of about 10 mg/mL up to about 250 mg/mL. Further, some embodiments disclose a composition comprising one or more benzodiazepine drugs or pharmaceutically-acceptable salts thereof in a concentration of about 20 mg/mL up to about 50 mg/mL.

Some embodiments disclose a carrier system that is about 50% to about 90% (w/w) Vitamin E and about 10% to about 50% (w/w) lower alcohol or lower alkyl glycol, or any combinations thereof. Some embodiments disclose a carrier system that is about 65% to about 75% (w/w) Vitamin E and about 25% to about 35% (w/w) lower alkyl alcohol or lower alkyl glycol, or any combinations thereof. Further, some embodiments disclose a carrier system that is about 70%

(w/w) Vitamin E and about 30% (w/w) lower alkyl alcohol or lower alkyl glycol, or any combinations thereof.

Some embodiments of the invention provide a method of administering the benzodiazepine drug composition to a patient. The preferred embodiment comprises use of diazepam. Some embodiments of the method disclose a dosage level of diazepam of about 1.0 mg to about 20.0 mg until achievement of the desired result. Other dosage levels disclose a dosage level of about 2.0 mg to about 15.0 mg until the desired result is achieved. Some embodiments disclose a dosage level of about 5.0 mg to about 10.0 mg until the desired result is achieved.

In some embodiments of the method, the dosage volume ranges from about 10 μL to about 200 μL. In some embodiments, the dosage volume ranges from about 20 μL to about 180 μL. Further, some embodiments disclose a dosage volume of about 50 μL to about 140 μL.

Formulation Process

In some embodiments, the composition for nasal administration is substantially free of benzodiazepine microparticles, nanoparticles or combinations thereof. In some embodiments, the composition is made by slowly warming or heating the Vitamin E until it is liquefied. Next, the one or more benzodiazepine drugs are added. The mixture is stirred and heated until the one or more benzodiazepine drugs dissolve or are substantially dissolved. Next, the one or more alcohols or glycols, or any combinations thereof, are added to the composition. This composition is stirred until a less viscous composition is achieved.

The aforementioned formulations are preferably sterile with a bacteria count of 10 below the allowable level on a per mL basis. Additionally, pathogens are preferably absent.

In some embodiments, the benzodiazepine drug is formulated as a microparticulate and/or nanoparticulate suspension of the benzodiazepine. Preparation of microparticulate and nanoparticulate benzodiazepine may be accomplished by methods such as milling, etc. Such methods are known to those skilled in the art.

In some embodiments, the benzodiazepine drug is formulated as a solution. It is considered an aspect of the invention that employment of microparticulate and/or nanoparticulate benzodiazepine drug during the process of preparing the formulation, can improve the overall solubility of the benzodiazepine drug in the solvent system.

Additional Active and Inactive Ingredients

Additionally, some embodiments of the compositions and methods of using the compositions comprise an additional ingredient in the composition selected from active ingredients. By way of non-limiting example, such active ingredients include insulin, calcitonins (for example porcine, human, salmon, chicken, or eel) and synthetic modifications thereof, enkephalins, LHRH and analogues (Nafarelin, Buserelin, Zolidex), GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone (solatotropir polypeptides or their derivatives (preferably with a molecular weight from 1000 to 300000), secretin, bradykinin antagonists, GRF (Growth releasing factor), THF, TRH (Thyrotropin releasing hormone), ACTH analogues, IGF (Insulin like growth factors), CGRP (Calcitorin gene related peptide) Atrial Natriuretic peptide, Vasopressin and analogues (DDAVP, Lypressin), Metoclopramide, Migraine treatment (Dihydroergotamine, Ergometrine, Ergotamine, Pizotizin), Nasal Vaccines (Particularly AIDS vaccines) FACTOR VIII, Colony Stimulating factors, G-CSF (granulocyte-colony stimulating factor), EPO (Erythropoitin) PTH (Parathyroid hormone) or pharmaceutically acceptable salts or combinations thereof.

Additionally, some embodiments of the compositions and methods of using the compositions comprise an additional ingredient in the composition selected from other anticonvulsants. By way of non-limiting example, such active ingredients include: paraldehyde; aromatic allylic alcohols (such as stiripentol); barbiturates (e.g. phenobarbitol, primidone, methylphenobarbital, metharbital and barbexaclone); bromides (such as potassium bromide); carbamates (such as felbamate); carboxamides (such as carbamazepine and oxcarbazepine); fatty acids (such as valproic acid, sodium valproate, and divalproex sodium, vigabatrin, progabide, tiagabine); fructose, topiramate, Gaba analogs (e.g. gabapentin and pregabalin); hydantoins (e.g. ethotoin, phenytoin, mephenytoin and fosphenytoin); oxazolidinediones (such as paramethadione, trimethadione, ethadione); propionates (e.g. beclamide), pyrimidinediones (e.g. primidone); pyrrolidines (e.g. brivaracetam, levetiracetam and seletracetam); succinimides (e.g. ethosuximide, phensuximide and mesuximide); sulfonamides (e.g. acetazolamide, sulthiame, methazolamide and zonisamide); triazines (such as lamotrigine); ureas (such as pheneturide, phenacemide); valproylamides (such as valpromide and valnoctamide); as well as other anticonvulsants or pharmaceutically acceptable salts or combinations thereof.

Additionally, some embodiments of the compositions and methods of using the compositions comprise an additional ingredient in the composition selected from other anticonvulsants. By way of non-limiting example, such active ingredients include: antibiotics and antimicrobial agents such as tetracyline hydrochloride, leucomycin, penicillin, penicillin derivatives, erythromycin, gentamicin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, active vitamin D and vitamin C; sex hormones; hypotensives; sedatives; anti-tumor agents; steroidal anti-inflammatory agents such as hydrocortisone, prednisone, fluticasone, prednisolone, triamcinolone, triamcinolone acetonide, dexamethasone, betamethasone, beclomethasone, and beclomethasone dipropionate; nonsteroidal anti-inflammatory agents such as acetaminophen, aspirin, aminopyrine, phenylbutazone, medanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents and antitussive-expectorant antasthmatic agents such as sodium chromoglycate, codeine phosphate, and isoproterenol hydrochloride or pharmaceutically acceptable salts or combinations thereof.

Additionally, some embodiments of the compositions and methods of using the compositions comprise an additional inactive ingredient in the composition. By way of non-limiting example, minor amounts of ingredients such as stabilizers, coloring agents, pH adjusters, buffering agents, preservatives such as agents which may prevent degradation, wetting agents, and flavoring agents may also be present. Examples of coloring agents include β-carotene, Red No. 2 and Blue No. 1. Examples of preservatives include stearic acid, ascorbyl stearate and ascorbic acid. Examples of corrigents include menthol and citrus perfume.

In some embodiments, the drug delivery system of the invention may advantageously comprise an absorption enhancer. The term "enhancer", means any material which acts to increase absorption across the mucosa and/or increases bioavailability. In some embodiments, such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect.

In some embodiments, preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. palmitoyl-dl-carnitine-chloride) is an alternative. In some embodiments, a suitable concentration is from 0.02 to 20% w/v.

In some embodiments, enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316-321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% w/v.

In some embodiments, the invention takes advantage of delivery of a drug incorporated into or onto a bioadhesive microsphere with an added pharmaceutical adjuvant applies to systems that contain active drug and mucolytic agent, peptidase inhibitors or non-drug polypeptide substrate singly or in combination. Suitably mucolytic agents are thiol-containing compounds such as N-acetylcysteine and derivatives thereof. Peptide inhibitors include actinonin, amastatin, bestatin, chloroacetyl-HOLeu-Ala-Gly-NH.sub.2, diprotin A and B, ebelactone A and B, E-64, leupeptin, pepstatin A, phisphoramidon, H-Thr-(tBu)-Phe-Pro-OH, aprotinin, kallikrein, chymostatin, benzamidine, chymotrypsin and trypsin. Suitable concentrations are from 0.01 to 10% w/v. The person skilled in the art will readily be able to determine whether an enhancer should be included.

Administration

In some embodiments, the administration of the composition comprises administering at least a portion of the therapeutically effective amount of the composition onto at least one mucosal membrane. In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

Alprazolam

The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

As a nasal formulation, alprazolam may be administered in 25 to 250 µL metered sprays. In some preferred embodiments, alprazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Diazepam

The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085, 3,109,843, 3,136,815 or 3,102,116, each of which is incorporated herein by reference in its entirety.

As a nasal formulation, diazepam may be administered in 25 to 250 µL metered sprays. In some preferred embodiments, diazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Flurazepam

The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. No. 3,567,710 or 3,299,053, each of which is incorporated herein by reference in its entirety.

As a nasal formulation, flurazepam may be administered in 25 to 250 µL metered sprays. In some preferred embodiments, flurazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Lorazepam

The dosage of Lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

As a nasal formulation, lorazepam may be administered in 25 to 250 µL metered sprays. In some preferred embodiments, lorazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Medazepam

The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

As a nasal formulation, medazepam may be administered in 25 to 250 µL metered sprays. In some preferred embodiments, medazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Mexazolam

The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

As a nasal formulation, mexazolam may be administered in 25 to 250 µL metered sprays. In some preferred embodiments, mexazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Midazolam

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. No. 4,280,957 or 5,831,089, each of which is incorporated herein by reference in its entirety.

As a nasal formulation, midazolam may be administered in 25 to 250 µL metered sprays. In some preferred embodiments, midazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Temazepam

The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. No. 3,340,253 or 3,374,225, each of which is incorporated herein by reference in its entirety.

As a nasal formulation, temazepam may be administered in 25 to 250 µL metered sprays. In some preferred embodiments, temazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Those skilled in the art will be aware that a systematic, therapeutically effective amount of benzodiazepine drugs for treating the aforementioned disorders will vary with age, size, weight, and general physical condition of the patient as well as the severity of the disease. Frequency of administration will likewise vary with the formulation of the composition and it can be adjusted so that any suitable number of doses per day may be used.

EXAMPLES

The invention will now be illustrated with reference to the following illustrative, non-limiting examples.

Example 1

A pharmaceutical composition comprising diazepam is prepared. It is formulated as a solution to be delivered via a nasal delivery device. The composition is used to treat or prevent seizures associated with epilepsy in adults. Treatment is administered either before or after a seizure has begun. If the patient is seizing, it is administered as 1 puff from any nasal delivery device (1 puff at 5.0 mg/puff (5.0 mg/0.1 mL and 0.1 mL/puff)) every 5 minutes until cessation of the seizure. However, it can be given as 1 puff per nostril in each nostril (2 puffs at 2.5 mg/puff (5.0 mg/0.1 mL and 0.05 mL/puff)) every 5 minutes until cessation of the seizure. The composition according to this example is set forth in the following table.

TABLE 1-1

| 5.0 mg/0.1 mL | Diazepam |
| 70.0 mg | α-tocopherol |
| 0.1 mL | ethanol (qs ad to 0.1 mL) |

Example 2

A pharmaceutical composition comprising diazepam is prepared. It is formulated as a solution to be delivered via a nasal delivery device. The composition is used to treat or prevent seizures associated with epilepsy in children. Treatment is administered either before or after a seizure has begun. If the patient is seizing, it is administered as 1 puff from any nasal delivery device (1 puff at 2.0 mg/puff (2.0 mg/0.1 mL and 0.1 mL/puff)). If the seizure fails to stop another dose may be administered after 5 minutes. However, it can be given as 1 puff per nostril in each nostril (2 puffs at 1.0 mg/puff (2.0 mg/0.1 mL and 0.05 mL/puff)). If the seizure fails to stop another dose may be administered after 5 minutes. The composition according to this example is set forth in the following table.

TABLE 2-1

| 2.0 mg/0.1 mL | Diazepam |
| 70.0 mg | α-tocopherol |
| 0.1 mL | ethanol (qs ad to 0.1 mL) |

Example 3—Formulation of Diazepam Solutions

In general, benzodiazepine solutions may be formulated by combining one or more natural or synthetic tocopherols or tocotrienols and one or more lower alcohols or glycols and mixing until a homogeneous mixture is formed, adding the benzodiazepine drug to the homogeneous mixture, heating and mixing the ingredients until the benzodiazepine is fully dissolved in the homogeneous mixture, cooling the mixture, and bringing the mixture to its final mass or volume with lower alcohol or glycol.

Two different diazepam solutions were formulated by the foregoing process. Vitamin E USP and dehydrated ethanol USP were combined in the amounts set forth in the following table and mixed to form a homogeneous mixture. Diazepam in the amounts set forth in the following table was then added to the homogeneous mixture. The ingredients were heated to 40-45° C. with mixing until the diazepam was fully dissolved, thereby forming a solution. The solution was cooled to 20-25° C., whereupon the solution was brought to its final target weight with dehydrated ethanol USP and the solution was mixed thoroughly to assure homogeneity. The solution was then sampled for in-process testing and packaged in 3 mL amber glass vials.

TABLE 3-1

Diazepam Solutions-70 mg/mL

| Component | Solution 00 (65% Vitamin E) Concentration (mg/mL) | Solution 02 (80% Vitamin E) Concentration (mg/mL) |
|---|---|---|
| Diazepam USP | 70.0 | 70.0 |
| Vitamin E USP | 650.0 | 800.0 |
| Dehydrated Ethanol USP | q.s. to 1 mL | q.s. to 1 mL |

Additional solutions of diazepam at varying concentrations are made in a similar manner, by varying the amount of diazepam and the relative amounts of Vitamin E and ethanol. Other benzodiazepine solutions are made by substituting one or more benzodiazepines for diazepam. Other ingredients, such as alkyl glycoside, can be added at a suitable step in the process (e.g. before or concurrently with the addition of benzodiazepine).

Example 4—Formulation of Diazepam Suspensions

In general, benzodiazepine suspensions are formulated by micronizing benzodiazepine and combining the benzodiazepine with a carrier. The carrier is prepared by combining one or more lower alcohols or glycols with water, adding a natural or synthetic tocopherol or tocotrienol, heating the mixture until the tocopherol or tocotrienol is dissolved, adding one or more parabens and mixing until the parabens are dissolved and cooling the carrier. Once the benzodiazepine is added to the carrier, additional excipients, such as surfactants, can optionally be added and dissolved in the carrier. The suspension is then brought up to its final mass or volume with water.

Two different diazepam suspensions were formulated by the foregoing general process. Two different diazepam particle sizes were prepared—A: a small particle size by prepared by high pressure micronization, and B: a large particle size prepared by low pressure micronization. The carrier was prepared by combining propylene glycol USP and purified water USP, then adding Vitamin E Polyethylene Glycols Succinate NF, then mixing and heating the combined ingredients to about 45° C. Mixing was continued until the Vitamin E Polyethylene Glycol Succinate was fully dissolved. The carrier was then cooled to 20-25° C. The micronized diazepam (A and B) was then added to the carrier with vigorous mixing until the diazepam was fully dispersed in the carrier. Polyvinylpyrrolidone Povidone USP/NF was then added to the mixture and mixed until fully dissolved. The suspension was then brought up to weight with purified water USP. The suspension was then mixed until homogeneous, sampled for in-process testing, and packaged in 3 mL amber glass bottles.

TABLE 4-1

Diazepam Suspension Formulations

| Component | Suspension 03 (200 mg/mL Diazepam) Concentration (mg/mL) | Suspension 01 (100 mg/mL Diazepam) Concentration (mg/mL) |
|---|---|---|
| Diazepam USP | 200.00 | 100.00 |
| Vitamin E Polyethylene Glycol Succinate NF | 100.0 | 100.0 |
| Methylparaben NF | 2.0 | 2.0 |
| Propylparaben NF | 0.5 | 0.5 |
| Propylene Glycol USP | 100.0 | 100.0 |
| Povidone USP/NF | 25.0 | 25.0 |
| Purified Water USP/EP | q.s. to 1 mL | q.s. to 1 mL |

Additional suspensions of diazepam at varying concentrations are made in a similar manner, by varying the amount of diazepam and optionally other excipients. Other benzodiazepine suspensions are made by substituting one or more benzodiazepines for diazepam. Other ingredients, such as alkyl glycoside, can be added at a suitable step in the process. For example, an alkylglycoside may be added to the carrier during compounding of the carrier, or may be added to the suspension mixture concurrently with or after addition of the povidone.

Example 5—Stability of Diazepam Solutions and Suspensions

Solutions 00 and 02 (Example 3) and Suspensions 01 and 03 (Example 4) were set up on stability at 25° C./60% RH, 30° C./65% RH and 40° C./75% RH. One batch each of four different formulations, packaged in 3-ml vials with screw-top closures, along with corresponding actuators, were set up at three storage conditions. They are listed in Table 1 with their corresponding Particle Sciences initial sample control numbers.

TABLE 5-1

Summary of PSI sample control numbers

| Formulation # | 25° C./60% RH | 30° C./65% RH | 40° C./75% RH |
|---|---|---|---|
| Solution 00-70 mg/ml solution, 65% Vitamin E | 083101.01 | 083101.02 | 083101.02 |
| Solution 02-70 mg/ml solution, 80% vitamin E | 083102.01 | 083102.02 | 083102.03 |
| Suspension 01-100 mg/mi suspension | 083103.01 | 083103.02 | 083103.03 |
| Suspension 03-200 mg/ml suspension | 083104.01 | 083104.02 | 083104.03 |

Samples were tested for spray content uniformity, spray volume, diazepam content, diazepam related substances, and methylparaben and propylparaben assay (suspension samples only). Unit weights were determined as per USP <755>.

Summaries of the average assay values and all other results are given in Tables 5-4, 5-5, 5-6 and 5-7. The results for the initial, 1-month and 3-month time points are also shown for comparison. Individual spray content uniformity results are given in Tables 5-8, 5-9, 5-10, 5-11, 5-12, 5-13, 5-14, and 5-15.

In general, all of the assays and the other results are similar to the initial data, with the exceptions of diazepam related compounds A and B.

Related compound A did not meet the specification of not more than (NMT) 0.01% for some samples (see Table 2). Related compound A has increased with time and temperature.

TABLE 5-2

Summary of related compound A T6M results

| Solution/Suspension # | 25° C./60% RH | 30° C./65% RH | 40° C./75% RH |
|---|---|---|---|
| Solution 00 | Meets specification | 0.058% | 0.051% |
| Solution 02 | Meets specification | Meets specification | Meets specification |
| Suspension 01 | 0.038% | 0.046% | 0.157% |
| Suspension 03 | 0.019% | 0.029% | 0.081% |

Related compound B is also increasing with time and temperature, and now fails specification of NMT 0.1% at 40° C. condition for both suspension and one solution formulation. Only formulation 2602 meets all impurity specifications.

TABLE 5-3

Summary of related compound B T6M results

| Solution/Suspension # | 25° C./60% RH | 30° C./65% RH | 40° C./75% RH |
|---|---|---|---|
| Solution 00 | Meets specification | Meets specification | 0.398% |
| Solution 02 | Meets specification | Meets specification | Meets specification |
| Suspension 01 | Meets specification | Meets specification | 0.289% |
| Suspension 03 | Meets specification | Meets specification | 0.123% |

TABLE 5-4

Summary of Solution 00 results

| Solution 00, 70 mg/ml, 65% Vitamin E | Specifications | Initial | 1 month 25° C./60 % RH | 1 month 30° C./65 % RH | 1 month 40° C./75 % RH | 3 month 25° C./60 % RH | 3 month 30° C./65 % RH | 3 month 40° C./75 % RH | 6 month 25° C./60 % RH | 6 month 30° C./65 % RH | 6 month 40° C./75 % RH |
|---|---|---|---|---|---|---|---|---|---|---|---|
| Description | Yellow to orange solution | Amber solution | Amber solution | Amber solution | Amber solution | Amber solution | Amber solution | Amber solution | Amber solution | Amber solution | Amber solution |
| Identification-UV | Conforms to reference std. UV and RT | pass | N/A | N/A | N/A | N/A | N/A | N/A | N/A | N/A | N/A |
| Assay Diazepam (%) | 90.0 to 110.0% | 100.1 | 100.3 | 93.9 | 98.8 | 96.3 | 96.9 | 101.2 | 97.5 | 94.6 | 100.6 |
| Impurities (%) [1] | | | | | | | | | | | |
| Nordazepam | NMT 0.3% | 0.005 | 0.01 | 0.014 | 0.019 | 0.013 | 0.013 | 0.013 | 0.013 | 0.013 | 0.013 |
| Related Compound B | NMT 0.1% | ND | 0.002 | 0.007 | 0.03 | 0.008 | 0.016 | 0.089 | 0.024 | 0.098 | 0.398 |
| Related Compound A | NMT 0.01% | 0.002 | 0.002 | 0.004 | 0.011 | 0.002 | 0.002 | 0.01 | 0.005 | 0.058 | 0.051 |
| Unknown | NMT 0.1% | 0.011 | 0.012 | 0.014 | 0.02 | 0.037 | 0.039 | 0.047 | 0.035 | 0.066 | 0.055 |
| Total | NMT 1.0% | 0.0 | 0.0 | 0.0 | 0.1 | 0.1 | 0.1 | 0.2 | 0.1 | 0.2 | 0.5 |
| Microbial Limits | Meets USP {61} | pass | N/A | N/A | N/A | N/A | N/A | N/A | pass | not tested | not tested |
| Fill weight (g) | report results | 1.108 | 1.105 | 1.111 | 1.112 | 1.109 | 1.109 | 1.113 | 1.103 | 1.111 | 1.109 |
| Fill volume (ml) | report results | 1.192 | 1.189 | 1.195 | 1.196 | 1.193 | 1.193 | 1.198 | 1.187 | 1.195 | 1.193 |
| Spray delivered (μl) | report results | 133.9 | 140.7 | 146.8 | 140.5 | 149.1 | 143.5 | 139.6 | 131.4 | not tested | 136.4 |
| Average Spray Content (%) | report results | 95.0 | 101.2 | 100.4 | 99.4 | 99.7 | 94.6 | 99.4 | 95.7 | not tested | 108.7 |
| Viscosity (Pa*s) | report results | 0.14 | 0.086 | 0.12 | 0.12 | 0.096 | 0.14 | 0.12 | 0.12 | 0.11 | 0.11 |

[1] LOQ is approximately 0.006%, LOD is approximately 0.002%. Results below LOQ are reported in this table for trending purposes.

TABLE 5-5

Summary of Solution 02 results

| Solution 02, 70 mg/mL, 65% Vitamin E | Specifications | Initial | 1 month 25° C./60 % RH | 1 month 30° C./65 % RH | 1 month 40° C./75 % RH | 3 month 25° C./60 % RH | 3 month 30° C./65 % RH | 3 month 40° C./75 % RH | 6 month 25° C./60 % RH | 6 month 30° C./65 % RH | 6 month 40° C./75 % RH |
|---|---|---|---|---|---|---|---|---|---|---|---|
| Description | Yellow to orange solution | Amber solution | Amber solution | Amber solution | Amber solution | Amber solution | Amber solution | Amber solution | Amber solution | Amber solution | Amber solution |
| Identification-UV | Conforms to reference std. UV and RT | pass | N/A | N/A | N/A | N/A | N/A | N/A | N/A | N/A | N/A |
| Assay Diazepam (%) | 90.0 to 110.0% | 100.5 | 94.9 | 96.2 | 103.3 | 98.0 | 97.2 | 99.6 | 97.0 | 94.3 | 100.3 |
| Impurities (%) [1] | | | | | | | | | | | |
| Nordazepam | NMT 0.3% | 0.003 | 0.004 | 0.005 | 0.006 | 0.005 | 0.005 | 0.006 | 0.005 | 0.004 | 0.005 |
| Related Compound B | NMT 0.1% | ND | 0.002 | 0.003 | 0.006 | 0.003 | 0.005 | 0.032 | 0.007 | 0.020 | 0.058 |
| Related Compound A | NMT 0.01% | 0.003 | 0.002 | 0.002 | 0.003 | 0.002 | 0.002 | 0.004 | 0.003 | 0.009 | 0.007 |
| Unknown | NMT 0.1% | 0.01 | 0.012 | 0.014 | 0.018 | 0.019 | 0.025 | 0.032 | 0.014 | 0.020 | 0.018 |
| Total | NMT 1.0% | 0.0 | 0.0 | 0.0 | 0.0 | 0.0 | 0.0 | 0.1 | 0.0 | 0.1 | 0.1 |
| Microbial Limits | Meets USP {61} | pass | N/A | N/A | N/A | N/A | N/A | N/A | pass | not tested | not tested |
| Fill weight (%) | report results | 1.135 | 1.117 | 1.128 | 1.123 | 1.116 | 1.133 | 1.137 | 1.124 | 1.133 | 1.127 |
| Fill volume (ml) | report results | 1.184 | 1.165 | 1.177 | 1.172 | 1.164 | 1.182 | 1.186 | 1.172 | 1.183 | 1.176 |
| Spray delivered (μl) | report results | 115.0 | 137.5 | 137.6 | 133.1 | 143.9 | 136.3 | 143.8 | 129.3 | not tested | 124.2 |
| Average Spray Content (%) | report results | 98.6 | 97.6 | 97.7 | 100.7 | 98.7 | 94.7 | 100.5 | 95.8 | not tested | 97.1 |
| Viscosity (Pa*s) | report results | 0.69 | 0.68 | 0.64 | 0.68 | 0.63 | 0.65 | 0.64 | 0.61 | 0.55 | 0.56 |

[1] LOQ is approximately 0.006%, LOD is approximately 0.002%. Results below LOQ are reported in this table for trending purposes.

TABLE 5-6

Summary of Suspension 01 results

| Suspension 01, 100 mg/ml | Specifications | Initial | 1 month 25° C./60 % RH | 1 month 30° C./65 % RH | 1 month 40° C./75 % RH | 3 month 25° C./60 % RH | 3 month 30° C./65 % RH | 3 month 40° C./75 % RH | 6 month 25° C./60 % RH | 6 month 30° C./65 % RH | 6 month 40° C./75 % RH |
|---|---|---|---|---|---|---|---|---|---|---|---|
| Description | Cloudy to white solution | White dispersion | White dispersion | White dispersion | White dispersion | White dispersion | White dispersion | White dispersion | White dispersion | pale yellow dispersion | yellow dispersion |
| Identification-UV | Conforms to reference std. UV and RT | Pass | N/A | N/A | N/A | N/A | N/A | N/A | N/A | N/A | N/A |
| Assay Diazepam (%) | 90.0 to 110.0% | 102.8 | 102.6 | 100.9 | 104.3 | 101.3 | 101.8 | 103.6 | 100.7 | 104.3 | 99.4 |
| Impurities (%) [1] | | | | | | | | | | | |
| Nordazepam | NMT 0.3% | ND | ND | ND | ND | ND | ND | ND | ND | ND | ND |
| Related Compound B | NMT 0.1% | ND | ND | ND | 0.004 | ND | 0.004 | 0.053 | 0.005 | 0.013 | 0.289 |
| Related Compound A | NMT 0.01% | ND | 0.01 | 0.02 | 0.034 | 0.026 | 0.036 | 0.08 | 0.038 | 0.046 | 0.157 |
| Unknown | NMT 0.1% | 0.008 | 0.008 | 0.008 | 0.008 | 0.008 | 0.007 | 0.007 | 0.008 | 0.007 | 0.018 |
| Total | NMT 1.0% | 0.0 | 0.0 | 0.0 | 0.0 | 0.0 | 0.0 | 0.1 | 0.1 | 0.1 | 0.5 |
| Methylparaben (%) | 80.0%-115.% | 97.7 | 100.2 | 92.1 | 100.3 | 101.4 | 100.6 | 101.6 | 106.0 | 103.2 | 103.2 |
| Propylparaben (%) | 80.0%-115.0% | 100.2 | 100.5 | 92.2 | 99.2 | 100.6 | 99 | 100 | 98.5 | 97.6 | 96.7 |

TABLE 5-6-continued

Summary of Suspension 01 results

| Suspension 01, 100 mg/ml | Specifi- cations | Initial | 1 month 25° C./60 % RH | 1 month 30° C./65 % RH | 1 month 40° C./75 % RH | 3 month 25° C./60 % RH | 3 month 30° C./65 % RH | 3 month 40° C./75 % RH | 6 month 25° C./60 % RH | 6 month 30° C./65 % RH | 6 month 40° C./75 % RH |
|---|---|---|---|---|---|---|---|---|---|---|---|
| Microbial Limits | Meets USP {61} | Pass | N/A | N/A | N/A | N/A | N/A | N/A | pass | not tested | not tested |
| Fill weight (g) | report results | 1.254 | 1.252 | 1.252 | 1.244 | 1.246 | 1.248 | 1.247 | 1.245 | 1.242 | 1.235 |
| Fill volume (ml) | report results | 1.198 | 1.196 | 1.196 | 1.188 | 1.191 | 1.193 | 1.191 | 1.190 | 1.187 | 1.180 |
| Spray delivered (μl) | report results | 132.5 | 131.2 | 126 | 123.9 | 137.6 | 137.8 | 136.3 | 140.0 | not tested | 137.6 |
| Average Spray Content (%) | report results | 92.2 | 94.2 | 91.1 | 89.9 | 101.5 | 100.4 | 95.3 | 101.8 | not tested | 95.94 |
| Viscosity (Pa*s) | report results | 0.0098 | 0.0098 | 0.0092 | 0.0090 | 0.0092 | 0.0093 | 0.0089 | 0.0082 | 0.0080 | 0.0092 |

[1] LOQ is approximately 0006%, LOD is approximately 0.002%. Results below LOQ are reported in this table for trending purposes.

TABLE 5-7

Summary of Suspension 03 results

| Suspension 03, 200 mg/mL | Specifi- cations | Initial | 1 month 25° C./60 % RH | 1 month 30° C./65 % RH | 1 month 40° C./75 % RH | 3 month 25° C./60 % RH | 3 month 30° C./65 % RH | 3 month 40° C./75 % RH | 6 month 25° C./60 % RH | 6 month 30° C./65 % RH | 6 month 40° C./75 % RH |
|---|---|---|---|---|---|---|---|---|---|---|---|
| Description | Cloudy to white dispersion | White dispersion | White dispersion | White dispersion | White dispersion | White dispersion | White dispersion | White dispersion | White dispersion | pale yellow dispersion | yellow dispersion |
| Identification- UV | Conforms to reference std. UV and RT | Pass | N/A | N/A | N/A | N/A | N/A | N/A | N/A | N/A | N/A |
| Assay Diazepam (%) | 90.0 to 110.0% | 100.7 | 101.2 | 98.9 | 101.6 | 102.6 | 103.6 | 103.1 | 100.5 | 98.9 | 100.1 |
| Impurities (%) [1] | | | | | | | | | | | |
| Nordazepam | NMT 0.3% | ND | ND | ND | ND | ND | ND | ND | ND | ND | ND |
| Related Compound B | NMT 0.1% | ND | ND | ND | ND | 0.002 | ND | 0.023 | 0.002 | 0.008 | 0.123 |
| Related Compound A | NMT 0.01% | ND | 0.005 | 0.01 | 0.017 | 0.017 | 0.012 | 0.039 | 0.019 | 0.029 | 0.081 |
| Unknown | NMT 0.1% | 0.008 | 0.008 | 0.008 | 0.008 | 0.008 | 0.008 | 0.008 | 0.008 | 0.007 | 0.008 |
| Total | NMT 1.0% | 0.0 | 0.0 | 0.0 | 0.0 | 0.0 | 0.0 | 0.1 | 0.0 | 0.0 | 0.2 |
| Methylparaben (%) | 80.0%- 115.% | 93.4 | 101.1 | 93.8 | 99.7 | 101.5 | 101.6 | 101.2 | 103.5 | 97.2 | 102.1 |
| Propylparaben (%) | 80.0% 115.0% | 95.6 | 100.2 | 94 | 98.4 | 100.1 | 101.3 | 99.2 | 97.1 | 91.9 | 95.9 |
| Microbial Limits | Meets USP {61} | Pass | N/A | N/A | N/A | N/A | N/A | N/A | pass | not tested | not tested |
| Fill weight (g) | report results | 1.276 | 1.28 | 1.259 | 1.272 | 1.279 | 1.279 | 1.276 | 1.280 | 1.262 | 1.260 |
| Fill volume (ml) | report results | 1.186 | 1.19 | 1.171 | 1.183 | 1.19 | 1.19 | 1.187 | 1.190 | 1.173 | 1.172 |
| Spray delivered (μl) | report results | 112.4 | 137.4 | 134.3 | 119.9 | 138.9 | 139.3 | 134.3 | 149.4 | not tested | 138.0 |
| Average Spray Content (%) | report results | 82.8 | 99.3 | 97.3 | 86.7 | 98.6 | 102.3 | 96.2 | 98.2 | not tested | 98.7 |
| Viscosity (Pa*s) | report results | 0.021 | 0.017 | 0.017 | 0.019 | 0.016 | 0.016 | 0.018 | 0.014 | 0.013 | 0.015 |

[1] LOQ is approximately 0.006%, LOD is approximately 0.002%. Results below LOQ are reported in this table for trending purposes.

TABLE 5-8

Solution 00 25° C./60% RH spray content uniformity results

| Sample | Weight Collected, g | Weight Actuated, g | Diazepam Recovered, mg | % Diazepam Recovered |
|---|---|---|---|---|
| 1 | 0.13061 | 0.13259 | 9.59355 | 97.89 |
| 2 | 0.13217 | 0.13451 | 9.78206 | 99.82 |
| 3 | 0.12365 | 0.13332 | 8.85797 | 90.39 |
| 4 | 0.12761 | 0.13072 | 9.39720 | 95.89 |
| 5 | 0.14702 | 0.15216 | 8.91438 | 90.96 |
| 6 | 0.13414 | 0.13702 | 9.22442 | 94.13 |
| 7 | 0.12959 | 0.13384 | 9.84590 | 100.47 |
| 8 | 0.12367 | 0.14603 | 8.88093 | 90.62 |
| 9 | 0.13367 | 0.13425 | 9.92610 | 101.29 |
| Average | 0.13135 | 0.13716 | 9.380 | 95.72 |
| St. Dev. | 0.0070 | 0.0071 | 0.4309 | 4.3970 |
| % RSD | 5.35 | 5.20 | 4.59 | 4.59 |

TABLE 5-9

Solution 00 40° C./75% RH spray content uniformity results

| Sample | Weight Collected, g | Weight Actuated, g | Diazepam Recovered, mg | % Diazepam Recovered |
|---|---|---|---|---|
| 1 | 0.14139 | 0.15111 | 10.57237 | 107.88 |
| 2 | 0.14731 | 0.15146 | 11.62831 | 118.66 |
| 3 | 0.14489 | 0.14684 | 10.94206 | 111.65 |
| 4 | 0.14237 | 0.14873 | 11.94883 | 121.93 |
| 5 | 0.12188 | 0.13415 | 9.78103 | 99.81 |
| 6 | 0.12756 | 0.13047 | 9.78347 | 99.83 |
| 7 | 0.13549 | 0.13841 | 10.45221 | 106.66 |
| 8 | 0.12323 | 0.12543 | 9.41177 | 96.04 |
| 9 | 0.14299 | 0.14517 | 11.35701 | 115.89 |
| Average | 0.13635 | 0.14131 | 10.653 | 108.70 |
| St. Dev. | 0.0097 | 0.0095 | 0.8884 | 9.0649 |
| % RSD | 7.14 | 6.76 | 8.34 | 8.34 |

TABLE 5-10

Solution 02 25° C./60% RH spray content uniformity results

| Sample | Weight Collected, g | Weight Actuated, g | Diazepam Recovered, mg | % Diazepam Recovered |
|---|---|---|---|---|
| 1 | 0.12280 | 0.12611 | 8.88043 | 90.62 |
| 2 | 0.13318 | 0.13549 | 9.55581 | 97.51 |
| 3 | 0.13260 | 0.13452 | 9.71837 | 99.17 |
| 4 | 0.12064 | 0.12305 | 9.48123 | 96.75 |
| 5 | 0.13215 | 0.13582 | 9.34463 | 95.35 |
| 6 | 0.13559 | 0.13790 | 9.48722 | 96.81 |
| 7 | 0.13158 | 0.13371 | 9.43613 | 96.29 |
| 8 | 0.13357 | 0.13495 | 9.79164 | 99.91 |
| 9 | 0.12165 | 0.12443 | 8.84732 | 90.28 |
| Average | 0.12931 | 0.13178 | 9.394 | 95.85 |
| St. Dev. | 0.0058 | 0.0056 | 0.3303 | 3.3701 |
| % RSD | 4.52 | 4.25 | 3.52 | 3.52 |

TABLE 5-11

Solution 02 40° C./75% RH spray content uniformity results

| Sample | Weight Collected, g | Weight Actuated, g | Diazepam Recovered, mg | % Diazepam Recovered |
|---|---|---|---|---|
| 1 | 0.12336 | 0.12563 | 9.02005 | 92.04 |
| 2 | 0.05723 | 0.05792 | 9.43076 | 96.23 |
| 3 | 0.13554 | 0.13908 | 9.93829 | 101.41 |
| 4 | 0.13619 | 0.13679 | 9.87755 | 100.79 |
| 5 | 0.13227 | 0.13414 | 9.64403 | 98.41 |
| 6 | 0.13331 | 0.13515 | 9.80808 | 100.08 |
| 7 | 0.13455 | 0.13844 | 9.31952 | 95.10 |
| 8 | 0.13314 | 0.13736 | 9.28106 | 94.70 |

TABLE 5-11-continued

Solution 02 40° C./75% RH spray content uniformity results

| Sample | Weight Collected, g | Weight Actuated, g | Diazepam Recovered, mg | % Diazepam Recovered |
|---|---|---|---|---|
| 9 | 0.13249 | 0.13387 | 9.32935 | 95.20 |
| Average | 0.12423 | 0.12649 | 9.517 | 97.11 |
| St. Dev. | 0.0254 | 0.0260 | 0.3148 | 3.2119 |
| % RSD | 20.45 | 20.57 | 3.31 | 3.31 |

TABLE 5-12

Suspension 01 25° C./60% RH spray content uniformity results

| Sample | Weight Collected, g | Weight Actuated, g | Diazepam Recovered, mg | % Diazepam Recovered |
|---|---|---|---|---|
| 1 | 0.12873 | 0.12999 | 12.85366 | 91.81 |
| 2 | 0.14011 | 0.14247 | 13.68122 | 97.72 |
| 3 | 0.14515 | 0.14757 | 14.09449 | 100.67 |
| 4 | 0.13205 | 0.13347 | 14.18775 | 101.34 |
| 5 | 0.14554 | 0.14743 | 14.48202 | 103.44 |
| 6 | 0.14473 | 0.14682 | 14.39897 | 102.85 |
| 7 | 0.13229 | 0.13411 | 14.87853 | 106.28 |
| 8 | 0.14357 | 0.14581 | 14.82712 | 105.91 |
| 9 | 0.14741 | 0.14940 | 14.86732 | 106.20 |
| Average | 0.13995 | 0.14190 | 14.252 | 101.80 |
| St. Dev. | 0.0070 | 0.0074 | 0.6602 | 4.7154 |
| % RSD | 5.03 | 5.18 | 4.63 | 4.63 |

TABLE 5-13

Suspension 01 40° C./75% RH spray content uniformity results

| Sample | Weight Collected, g | Weight Actuated, g | Diazepam Recovered, mg | % Diazepam Recovered |
|---|---|---|---|---|
| 1 | 0.14411 | 0.14869 | 13.04770 | 93.20 |
| 2 | 0.14066 | 0.14151 | 13.23277 | 94.52 |
| 3 | 0.13012 | 0.13485 | 13.78126 | 98.44 |
| 4 | 0.14667 | 0.14879 | 13.36970 | 95.50 |
| 5 | 0.14294 | 0.14338 | 12.54309 | 89.59 |
| 6 | 0.13797 | 0.14253 | 13.25396 | 94.67 |
| 7 | 0.13374 | 0.13594 | 13.41984 | 95.86 |
| 8 | 0.12388 | 0.12559 | 14.34944 | 102.50 |
| 9 | 0.13790 | 0.14011 | 13.88564 | 99.18 |
| Average | 0.13755 | 0.14015 | 13.431 | 95.94 |
| St. Dev. | 0.0073 | 0.0073 | 0.5223 | 3.7310 |
| % RSD | 5.28 | 5.19 | 3.89 | 3.89 |

TABLE 5-14

Suspension 03 25° C./60% RH spray content uniformity results

| Sample | Weight Collected, g | Weight Actuated, g | Diazepam Recovered, mg | % Disazepam Recovered |
|---|---|---|---|---|
| 1 | 0.13604 | 0.13897 | 25.93418 | 92.62 |
| 2 | 0.14608 | 0.14792 | 26.21721 | 93.63 |
| 3 | 0.15425 | 0.15425 | 30.05570 | 107.34 |
| 4 | 0.14728 | 0.14910 | 25.78804 | 92.10 |
| 5 | 0.15352 | 0.15493 | 26.60721 | 95.03 |
| 6 | 0.15242 | 0.15401 | 29.51030 | 105.39 |
| 7 | 0.15118 | 0.15254 | 28.43104 | 101.54 |
| 8 | 0.15322 | 0.15556 | 28.03664 | 100.13 |

TABLE 5-14-continued

Suspension 03 25° C./60% RH spray content uniformity results

| Sample | Weight Collected, g | Weight Actuated, g | Diazepam Recovered, mg | % Disazepam Recovered |
|---|---|---|---|---|
| 9 | 0.15197 | 0.15393 | 26.82906 | 95.82 |
| Average | 0.14941 | 0.15125 | 27.490 | 98.18 |
| St. Dev. | 0.0057 | 0.0053 | 1.5812 | 5.6472 |
| % RSD | 3.79 | 3.50 | 5.75 | 5.75 |

TABLE 5-15

Suspension 03 40° C./75% RH spray content uniformity results

| Sample | Weight Collected, g | Weight Actuated, g | Diazepam Recovered, mg | % Disazepam Recovered |
|---|---|---|---|---|
| 1 | 0.13574 | 0.13797 | 28.14588 | 100.52 |
| 2 | 0.13639 | 0.13803 | 27.04437 | 96.59 |
| 3 | 0.14082 | 0.14195 | 26.78985 | 95.68 |
| 4 | 0.12962 | 0.13249 | 29.07192 | 103.83 |
| 5 | 0.12518 | 0.12683 | 27.39785 | 97.85 |
| 6 | 0.14423 | 0.14541 | 28.50133 | 101.79 |
| 7 | 0.13922 | 0.14096 | 27.34617 | 97.66 |
| 8 | 0.14146 | 0.14313 | 27.17415 | 97.05 |
| 9 | 0.14902 | 0.15344 | 27.20939 | 97.18 |
| Average | 0.13796 | 0.14002 | 27.631 | 98.68 |
| St. Dev. | 0.0073 | 0.0076 | 0.7642 | 2.7294 |
| % RSD | 5.28 | 5.43 | 2.77 | 2.77 |

Example 6

All of the solutions and suspensions described in Examples 3 and 4 are formulated as described in Examples 3 and 4, with the addition of a suitable amount of an alkyl glycoside, as described herein, such as dodecyl maltoside, tetradecyl maltoside, sucrose dodecanoate, sucrose monostearate, sucrose distearate, and/or combinations of two or more thereof, or marketed as Intravail® by Aegis Therapeutics, San Diego, Calif. The solutions and suspensions with added alkyl glycoside may then be put up on stability as described in Example 5, mutatis mutandis.

Example 7

The solutions and suspensions of Examples 3, 4 and 6 are evaluated for pharmacokinetics in a suitable animal model, such as in mice, rats, rabbits or dogs. First each animal (e.g. rabbit) is administered an amount of a benzodiazepine drug intravenously. The amount of intravenously dosed benzodiazepine drug is selected to be less, e.g. roughly half, of what is considered an effective dose administered nasally. For example, the intravenous dose of diazepam administered to rabbits is about 0.05 to about 0.2 mg/kg, e.g. about 0.1 mg/kg. Blood is collected immediately before administration and at specific time points post-administration. Plasma blood levels of the drug are assayed for each of the blood samples. After at least a one day washout period, each animal is administered, intranasally, an amount of a solution or suspension as described in Examples 3, 4 and 6. Blood is collected immediately before administration and at substantially the same specific time points as the IV dose post-administration. Pharmacokinetic curves (blood plasma concentration of drug versus time) are constructed for the intravenous route of administration and for each of the solutions and suspensions administered by the intranasal administration route.

Toxicity is assessed by known means. In particular, histological samples are collected from the nasal mucosal tissues of the test animals. Other toxological methods are optionally employed as well.

Example 8

The solutions and suspensions of Examples 3, 4 and 6 are evaluated for their ability to deliver drug across the blood brain barrier in a suitable animal model, such as in mice, rats, rabbits or dogs. Each animal is administered, intranasally, an amount of a solution or suspension as described in Examples 3, 4 and 6, with the solution or suspension optionally containing an imaging agent, such as a dye, that may be used as a proxy for determining the ability of the drug to cross the blood brain barrier. The drug or imaging agent is detected at selected time points after administration of the suspension or solution to determine how well the drug or imaging agent crosses the blood brain barrier. These results may be compared with analogous result obtained with an intravenous solution containing the drug or imaging agent.

Example 9

The above-described solutions and/or suspensions can be evaluated for pharmacokinetics in humans. Normal, healthy human test subjects are administered an amount of the drug intravenously. The amount chosen for intravenous administration may be any amount, but is conveniently a dose that is considered effective in treating seizure in humans. For example, an IV dose of diazepam administered to humans may be in the range of 1 to 15 mg, e.g. about 7.5 mg. Blood is collected immediately before administration and at selected time points after administration. Plasma blood levels of the drug are assayed for each of the blood samples. After at least a one day washout period, each subject is administered, intranasally, an amount of a solution or suspension as described herein. Blood is collected immediately before administration and at substantially the same time points after administration as the intravenous time points. Pharmacokinetic curves (blood plasma concentration of drug versus time) are constructed for the intravenous and intranasal administration routes.

Example 10

The above-described solutions and/or suspensions can be evaluated for efficacy in a suitable animal model. Briefly, for each dose of suspension or solution to be tested, a test animal is stimulated with a seizure inducing stimulus. The stimulus may be light, sound, chemical or other stimulus effective to induce seizure in the model animal. Once the animal has begun to seize, a solution or suspension as described herein is administered intranasally to the animal. The efficacy of the dose of the solution and/or suspension is evaluated based upon the animal's response to the test dose. This procedure is repeated through sufficient iterations, and at sufficient numbers of doses, to identify a dose that is considered effective to treat seizure by intranasal administration of the drug.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical solution for nasal administration consisting of:
   diazepam or a pharmaceutically acceptable salt thereof;
   one or more natural or synthetic tocopherols or tocotrienols, or any combinations thereof, in an amount from 30% to 95% (w/w);
   ethanol and benzyl alcohol in a combined amount from 10% to 70% (w/w); and
   n-dodecyl beta-D-maltoside.

2. The pharmaceutical solution of claim 1, wherein the diazepam or pharmaceutically acceptable salt thereof is present in the pharmaceutical solution in a concentration from 1 to 20% (w/v).

3. The pharmaceutical solution of claim 1, wherein the diazepam or pharmaceutically acceptable salt thereof is present in the pharmaceutical solution in a concentration from 10 mg/mL to 250 mg/mL.

4. The pharmaceutical solution of claim 3, wherein the diazepam or pharmaceutically acceptable salt thereof is present in the pharmaceutical solution in a concentration from 20 mg/mL to 50 mg/mL.

5. The pharmaceutical solution of claim 1, wherein the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, and any combinations thereof.

6. The pharmaceutical solution of claim 1, wherein the one or more natural or synthetic tocopherols or tocotrienols, or any combinations thereof, is in an amount from 45% to 85% (w/w).

7. The pharmaceutical solution of claim 6, wherein the one or more natural or synthetic tocopherols or tocotrienols, or any combinations thereof, is in an amount from 60% to 75% (w/w).

8. The pharmaceutical solution of claim 1, wherein the ethanol and benzyl alcohol is in a combined amount from 15% to 55% (w/w).

9. The pharmaceutical solution of claim 8, wherein the ethanol and benzyl alcohol is in a combined amount from 25% to 40% (w/w).

10. The pharmaceutical solution of claim 1, wherein the solution consists of diazepam, vitamin E, ethanol, benzyl alcohol, and n-dodecyl beta-D-maltoside.

11. A pharmaceutical solution for nasal administration consisting of:
    diazepam or a pharmaceutically acceptable salt thereof;
    one or more natural or synthetic α-tocopherols, or any combinations thereof, in an amount from 30% to 95% (w/w);
    ethanol and benzyl alcohol in a combined amount from 10% to 70% (w/w); and
    n-dodecyl beta-D-maltoside.

12. The pharmaceutical solution of claim 11, wherein the diazepam or pharmaceutically acceptable salt thereof is present in the pharmaceutical solution in a concentration from 1 to 20% (w/v).

13. The pharmaceutical solution of claim 11, wherein the diazepam or pharmaceutically acceptable salt thereof is present in the pharmaceutical solution in a concentration from 10 mg/mL to 250 mg/mL.

14. The pharmaceutical solution of claim 13, wherein the diazepam or pharmaceutically acceptable salt thereof is present in the pharmaceutical solution in a concentration from 20 mg/mL to 50 mg/mL.

15. The pharmaceutical solution of claim 11, wherein the one or more natural or synthetic α-tocopherols, or any combinations thereof is in an amount from 45% to 85% (w/w).

16. The pharmaceutical solution of claim 15, wherein the one or more natural or synthetic α-tocopherols, or any combinations thereof is in an amount from 60% to 75% (w/w).

17. The pharmaceutical solution of claim 11, wherein the ethanol and benzyl alcohol is in a combined amount from 15% to 55% (w/w).

18. The pharmaceutical solution of claim 17, wherein the ethanol and benzyl alcohol is in a combined amount from 25% to 40% (w/w).

* * * * *